US011753680B2

(12) United States Patent
Sarwal et al.

(10) Patent No.: US 11,753,680 B2
(45) Date of Patent: Sep. 12, 2023

(54) METHODS OF PREPARING A BIOFLUID SAMPLE FOR DETECTION OF KIDNEY INJURY

(71) Applicant: The Regents of the University of California, Oakland, CA (US)

(72) Inventors: Minnie M. Sarwal, San Francisco, CA (US); Tara K. Sigdel, San Francisco, CA (US); Joshua Y. Yang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/738,988

(22) Filed: May 6, 2022

(65) Prior Publication Data
US 2022/0333182 A1 Oct. 20, 2022

Related U.S. Application Data

(63) Continuation of application No. 17/498,489, filed on Oct. 11, 2021, now Pat. No. 11,505,822, which is a continuation of application No. 17/376,919, filed on Jul. 15, 2021, which is a continuation of application No. 16/325,385, filed as application No. PCT/US2017/047372 on Aug. 17, 2017, now Pat. No. 11,124,824.

(60) Provisional application No. 62/376,299, filed on Aug. 17, 2016.

(51) Int. Cl.
| C12Q 1/6883 | (2018.01) |
| G01N 33/70 | (2006.01) |
| G01N 33/68 | (2006.01) |
| G01N 33/53 | (2006.01) |
| C12Q 1/6853 | (2018.01) |
| C12Q 1/6827 | (2018.01) |
| G16H 10/40 | (2018.01) |
| C12Q 1/6813 | (2018.01) |
| C12Q 1/6876 | (2018.01) |

(52) U.S. Cl.
CPC ......... *C12Q 1/6853* (2013.01); *C12Q 1/6813* (2013.01); *C12Q 1/6827* (2013.01); *C12Q 1/6876* (2013.01); *C12Q 1/6883* (2013.01); *G01N 33/53* (2013.01); *G01N 33/68* (2013.01); *G01N 33/6827* (2013.01); *G01N 33/6839* (2013.01); *G16H 10/40* (2018.01); *C12Q 2600/112* (2013.01); *C12Q 2600/118* (2013.01); *C12Q 2600/154* (2013.01); *C12Q 2600/158* (2013.01); *G01N 33/70* (2013.01); *G01N 2800/245* (2013.01); *G01N 2800/347* (2013.01)

(58) Field of Classification Search
CPC ............ C12Q 1/6883; C12Q 2600/154; C12Q 2600/158; G16H 10/40; G01N 33/53; G01N 33/6827; G01N 33/70
See application file for complete search history.

(56) References Cited

U.S. PATENT DOCUMENTS

| 5,849,517 A | 12/1998 | Ryan |
| 5,922,544 A | 7/1999 | Miyai et al. |
| 8,404,444 B2 | 3/2013 | Zhang et al. |
| 10,982,272 B2 | 4/2021 | Sarwal et al. |
| 10,995,368 B2 | 5/2021 | Sarwal et al. |
| 11,124,824 B2 | 9/2021 | Sarwal et al. |
| 11,505,822 B2 | 11/2022 | Sarwal et al. |
| 2005/0069902 A1 | 3/2005 | Sinha et al. |
| 2010/0209930 A1 | 8/2010 | Fernando |
| 2011/0027771 A1 | 2/2011 | Deng |
| 2011/0111410 A1 | 5/2011 | Ryan et al. |
| 2011/0143348 A1 | 6/2011 | Tomigahara et al. |
| 2011/0300608 A1 | 12/2011 | Ryan et al. |
| 2012/0283128 A1 | 11/2012 | Anderberg et al. |
| 2016/0024581 A1 | 1/2016 | Sarwal et al. |
| 2019/0211385 A1 | 7/2019 | Sarwal et al. |
| 2020/0032331 A1 | 1/2020 | Sarwal et al. |
| 2021/0340610 A1 | 11/2021 | Sarwal et al. |

FOREIGN PATENT DOCUMENTS

| JP | 0821041 B2 | 3/1996 |
| JP | 2010017178 A | 1/2010 |
| JP | 2012108538 A | 6/2012 |
| JP | 2016512698 A | 5/2016 |
| JP | 2016520293 A | 7/2016 |
| WO | 9621041 A1 | 7/1996 |
| WO | 2006128192 A2 | 11/2006 |
| WO | 2011057184 A1 | 5/2011 |
| WO | 2011075744 A1 | 6/2011 |

(Continued)

OTHER PUBLICATIONS

"CXCL 10 Gene", Genecards, Available online at: https://www.genecards.org/cgi-bin/carddisp.pl?gene=CXCL10, Accessed from Internet on May 11, 2020, 27 pages.

(Continued)

*Primary Examiner* — Diana B Johannsen
(74) *Attorney, Agent, or Firm* — Kilpatrick Townsend & Stockton, LLP

(57) ABSTRACT

Provided herein is the use of measurements of cell-free DNA, protein, and/or metabolite found in biofluid (e.g., urine) for identifying and treating organ injury. Provided herein are methods and compositions for monitoring, detecting, quantifying, and treating kidney injury in subjects suffering from or suspected of having an altered renal status by measuring amounts of cfDNA and one or more other markers, such as inflammation markers, apoptosis markers, protein, and DNA methylation.

10 Claims, 19 Drawing Sheets
Specification includes a Sequence Listing.

(56) References Cited

FOREIGN PATENT DOCUMENTS

| WO | 2013173493 A1 | 11/2013 |
|---|---|---|
| WO | 2014029791 A1 | 2/2014 |
| WO | 2014029792 A1 | 2/2014 |
| WO | 2014074501 A1 | 5/2014 |
| WO | 2014145232 A2 | 9/2014 |
| WO | 2014146780 A1 | 9/2014 |
| WO | 2015035177 A1 | 3/2015 |
| WO | 2015159292 A2 | 10/2015 |
| WO | 2015161880 A1 | 10/2015 |
| WO | 2016007755 A1 | 1/2016 |
| WO | 2018031903 A1 | 2/2018 |
| WO | 2018035340 | 2/2018 |

OTHER PUBLICATIONS

U.S. Appl. No. 16/325,385, Non-Final Office Action, dated Mar. 30, 2021, 16 pages.
U.S. Appl. No. 16/325,385, Notice of Allowance, dated Jul. 22, 2021, 9 pages.
U.S. Appl. No. 16/597,782, Advisory Action, dated Dec. 3, 2020, 5 pages.
U.S. Appl. No. 16/597,782, Advisory Action, dated Nov. 4, 2020, 7 pages.
U.S. Appl. No. 16/597,782, Final Office Action, dated Aug. 12, 2020, 26 pages.
U.S. Appl. No. 16/597,782, Non-Final Office Action, dated Feb. 3, 2021, 21 pages.
U.S. Appl. No. 16/597,782, Non-Final Office Action, dated Feb. 14, 2020, 32 pages.
U.S. Appl. No. 16/597,782, Notice of Allowance, dated Mar. 5, 2021, 11 pages.
U.S. Appl. No. 17/065,417, Non-Final Office Action, dated Jan. 27, 2021, 19 pages.
U.S. Appl. No. 17/065,417, Notice of Allowance, dated Mar. 10, 2021, 10 pages.
U.S. Appl. No. 17/498,489, Final Office Action, dated Apr. 27, 2022, 14 pages.
U.S. Appl. No. 17/498,489, Non-Final Office Action, dated Jan. 21, 2022, 14 pages.
Batzer et al., "Alu Repeats and Human Genomic Diversity", Nature Reviews—Genetics; Nature Publishing Group, vol. 3, May 2002, pp. 370-379.
Bellomo et al., "Acute Kidney Injury", Lancet, vol. 380, Aug. 25, 2012, pp. 756-766.
Cannas et al., "Implications of Storing Urinary DNA from Different Populations for Molecular Analyses", Public Library of Science One, vol. 4, No. 9, Sep. 10, 2009, pp. 1-8.
Das et al., "Effects of a Novel Cell Stabilizing Reagent on DNA Amplification by PCR as Compared to Traditional Stabilizing Reagents", Acta Histochemica, vol. 116, No. 1, Jan. 2014, pp. 55-60.
De Vlaminck et al., "Noninvasive Monitoring of Infection And Rejection After Lung Transplantation", Proceedings of the National Academy of Sciences, vol. 112, No. 43, Oct. 27, 2015, pp. 13336-133341.
Application No. EP17842131.9, Extended European Search Report, dated Jun. 25, 2020, 14 pages.
EP17842131.9, "Partial Supplementary European Search Report", dated Mar. 23, 2020, 17 pages.
Application No. EP21152914.4, Extended European Search Report, dated Jun. 9, 2021, 13 pages.
Hu et al., "Noninvasive Detection of Acute and Chronic Injuries in Human Renal Transplant by Elevation of Multiple Cytokines/Chemokines in Urine", Transplantation, vol. 87, No. 12, Jun. 27, 2009, pp. 1814-1820.
Jin et al., "Examination of the Specificity of DNA Methylation Profiling Techniques Toward 5-Methylcytosine and 5-Hydroxymethylcytosine", Nucleic Acids Research, vol. 38, No. 11, Apr. 2010, pp. 1-7.

McPherson et al., "A Physical Map of the Human Genome", The International Human Genome Mapping Consortium, Nature, vol. 409, Feb. 15, 2001, pp. 934-941.
Mehta et al., ""WTC 06" Quantitative Detection of Promoter Hypermethylation as a Biomarker of Acute Kidney Injury During Transplantation", Transplantation Proceedings, vol. 38, No. 10, Dec. 2006, pp. 3420-3426.
Mohamed et al., "Kidney Damage Biomarkers Detect Acute Kidney Injury But Only Functional Markers Predict Mortality After Paraquat Ingestion", Toxicology Letters, vol. 237, No. 2, Sep. 2, 2015, 41 pages.
Moreira et al., "Cell-Free DNA as a Noninvasive Acute Rejection Marker in Renal Transplantation", Clinical Chemistry, vol. 55, No. 11, Nov. 2009, pp. 1958-1966.
Ozer et al., "A Panel of Urinary Biomarkers to Monitor Reversibility of Renal Injury and a Serum Marker with Improved Potential to Assess Renal Function", Nature Biotechnology, vol. 28, No. 5, May 10, 2010, pp. 486-494.
Application No. PCT/US2017/047372, International Preliminary Report on Patentability, dated Feb. 28, 2019, 8 pages.
Application No. PCT/US2017/047372, International Search Report and Written Opinion, dated Jan. 18, 2018, 12 pages.
PCT/US2017/047372, "Invitation to Pay Additional Fees And, Where Applicable, Protest Fee", dated Nov. 17, 2017, 2 pages.
Ralla et al., "Nucleic Acid-Based Biomarkers In Body Fluids Of Patients With Urologic Malignancies", Critical Reviews in Clinical Laboratory Sciences, vol. 51, No. 4, May 29, 2014, pp. 200-231.
Sacreas et al., "The Common Rejection Module in Chronic Rejection Post Lung Transplantation", PLoS One, vol. 13, No. 10, Oct. 5, 2018, pp. 1-16.
Sigdel et al., "A Computational Gene Expression Score for Predicting Immune Injury in Renal Allografts", PLoS One, vol. 10, No. 9, Sep. 14, 2015, pp. 1-10.
Sigdel et al., "A Rapid Noninvasive Assay for the Detection of Renal Transplant Injury", Transplantation, vol. 96, No. 1, Jul. 15, 2013, 10 pages.
Sigdel et al., "A Urinary Common Rejection Module (uCRM) Score for Non-Invasive Kidney Transplant Monitoring", PLoS One, vol. 14, No. 7, Jul. 31, 2019, pp. 1-15.
Sigdel et al., "Cell-Free DNA as a Measure of Transplant Injury", Clinical Transplants, Jan. 2012, pp. 201-205.
Sigdel et al., "Mining the Human Urine Proteome for Monitoring Renal Transplant Injury", Kidney International, vol. 89, No. 6, Jun. 2016, 18 pages.
Sigdel et al., "Optimizing Detection of Kidney Transplant Injury by Assessment of Donor-Derived Cell-Free DNA via Massively Multiplex PCR", Journal of Clinical Medicine, vol. 8, No. 1, Dec. 23, 2018, pp. 1-17.
Spivey et al., "Gene Expression Profiling in Acute Allograft Rejection: Challenging the Immunologic Constant of Rejection Hypothesis", Journal of Translational Medicine, vol. 9, No. 174, Oct. 12, 2011, pp. 1-22.
Vaara et al., "Urinary Biomarkers Indicative of Apoptosis and Acute Kidney Injury in the Critically Ill", PLOS ONE, vol. 11, No. 2, Feb. 26, 2016, 13 pages.
Vaidya et al., "Urinary Biomarkers for Sensitive and Specific Detection of Acute Kidney Injury in Humans", Clinical and Translational Science, vol. 1, No. 3, Dec. 2008, pp. 200-208.
Wang et al., "Computational Models for Transplant Biomarker Discovery", Frontiers in Immunology, vol. 6, Sep. 8, 2015, pp. 1-9.
Watson et al., "A Novel Multi-Biomarker Assay for Non-Invasive Quantitative Monitoring of Kidney Injury", Journal of Clinical Medicine, vol. 8, No. 4, Apr. 12, 2019, pp. 1-17.
Wright, "Receiver Operating Characteristics Curves", Encyclopedia of Statistics in Behavioral Science, vol. 4, Oct. 15, 2005, 5 pages.
Yang et al., "A Urine Score for Noninvasive Accurate Diagnosis and Prediction of Kidney Transplant Rejection", Science Translational Medicine, vol. 12, No. 535, Mar. 18, 2020, pp. 1-10.
Yang et al., "Cell-Free DNA and CXCL10 Derived from Bronchoalveolar Lavage Predict Lung Transplant Survival", Journal of Clinical Medicine, vol. 8, No. 2, Feb. 13, 2019, pp. 1-9.

(56) References Cited

OTHER PUBLICATIONS

Yang et al., "Noninvasive Urinary Monitoring of Progression in IgA Nephropathy", International Journal of Molecular Sciences, vol. 20, No. 18, Sep. 10, 2019, pp. 1-10.
Yang et al., "Non-Radiological Assessment of Kidney Stones Using the Kidney Injury Test (KIT), a Spot Urine Assay", BJU International, vol. 125, No. 5, May 2020, pp. 732-738.
Zhang et al., "Early Upsurge of Cell Free Alu DNA Predicts Declining Long-Term Graft Survival", American Journal of Transplantation, vol. 11, Apr. 2011, 3 pages.
U.S. Appl. No. 17/376,919, Non-Final Office Action, dated Mar. 23, 2023, 22 pages.
Cook et al., "Synthesis and Hybridization of a Series of Biotinylated Oligonucleotides", Nucleic Acids Research, vol. 16, Issue 9, 1988, pp. 4077-4095.

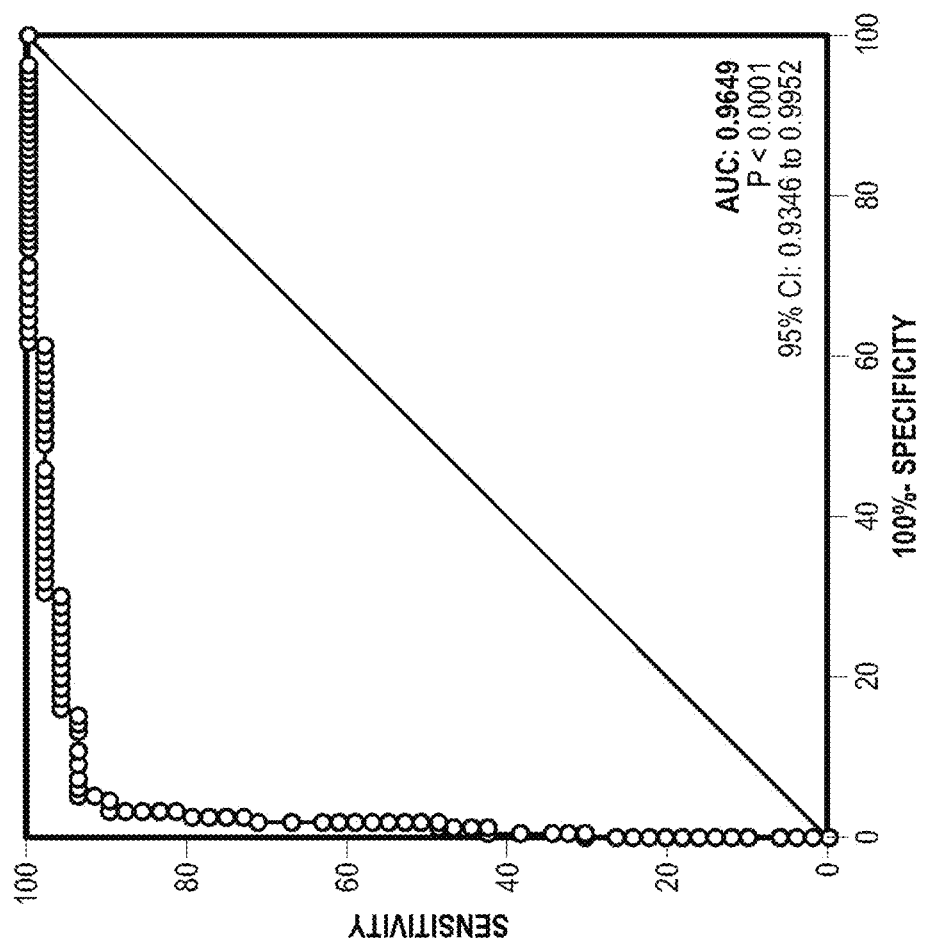
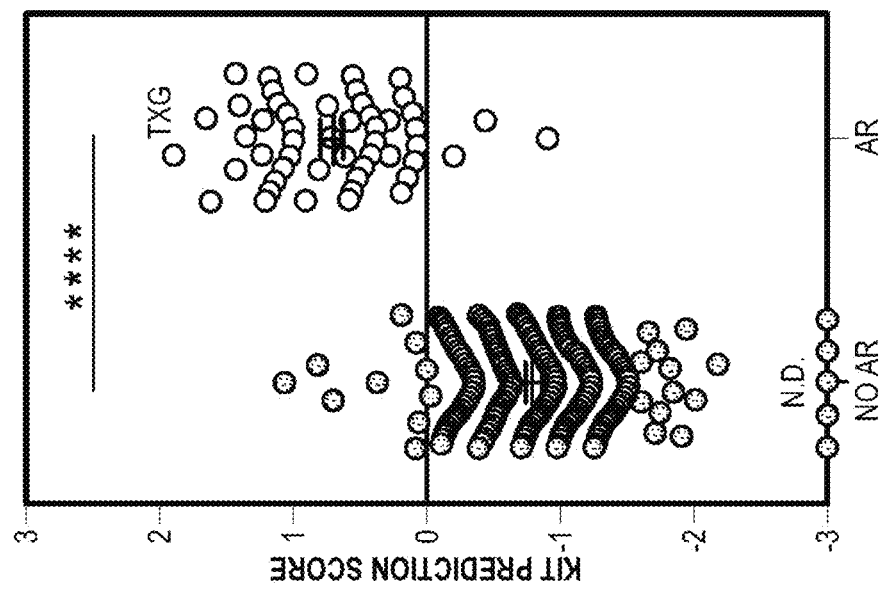
FIG. 5B
FIG. 5A

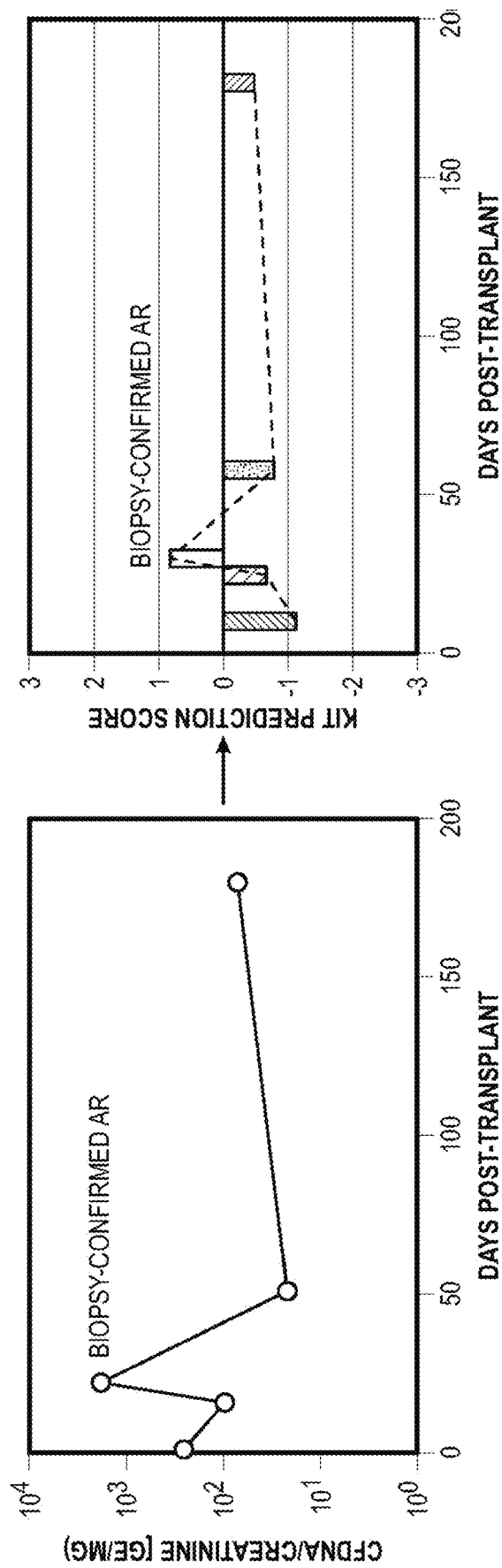

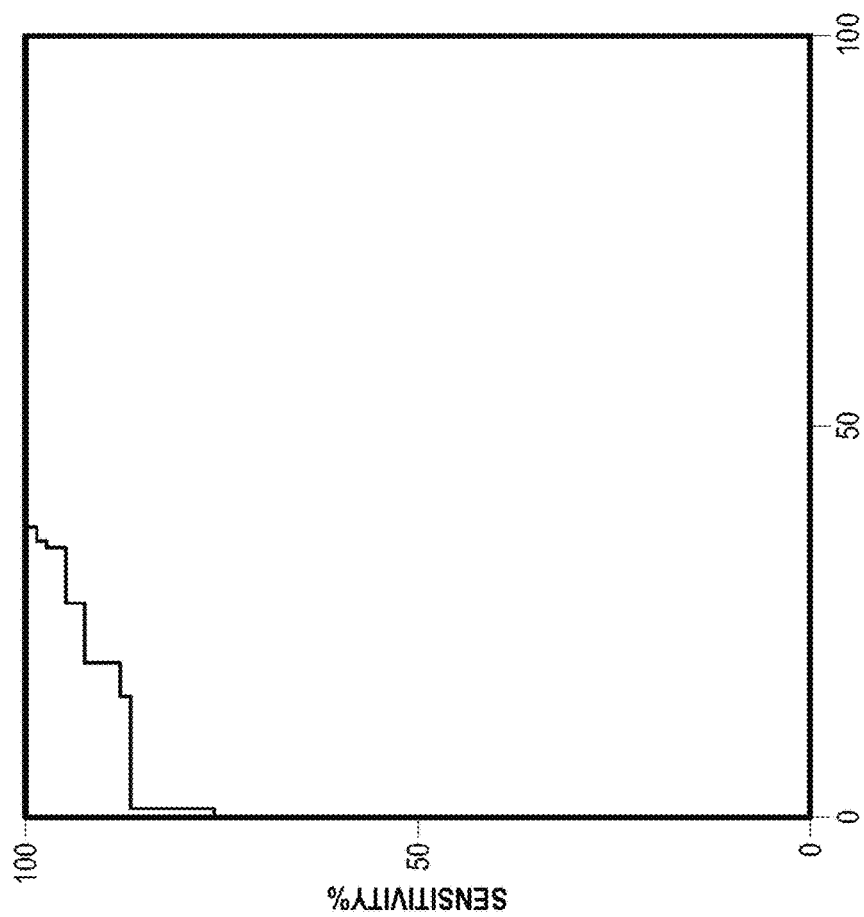
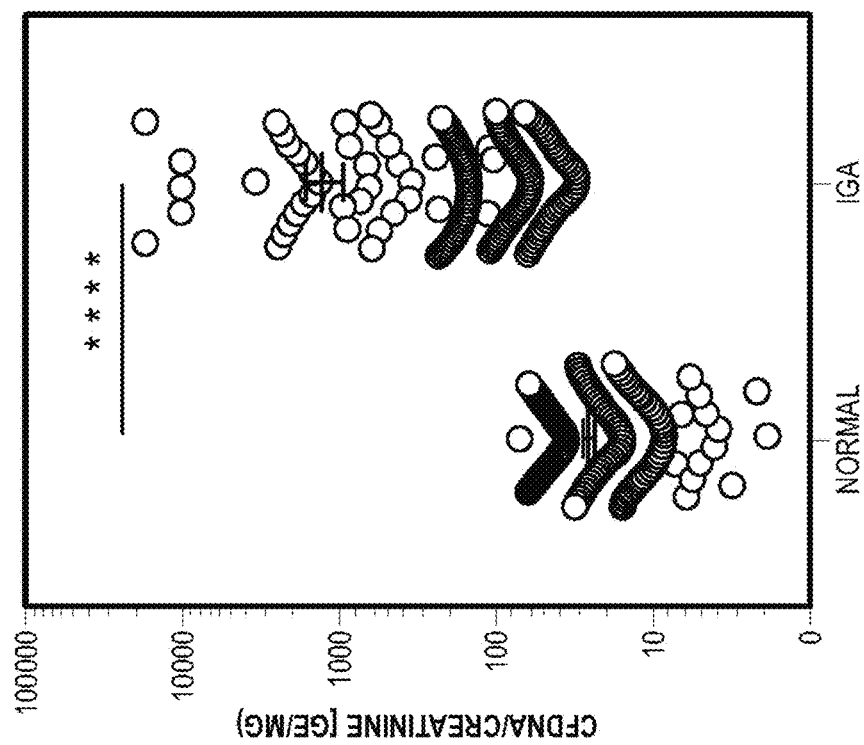
FIG. 10B
FIG. 10A

SEQUENCE LISTING

```
<160> NUMBER OF SEQ ID NOS: 2

<210> SEQ ID NO 1
<211> LENGTH: 290
<212> TYPE: DNA
<213> ORGANISM: Homo sapiens

<400> SEQUENCE: 1
ggccgggcgc ggtggctcac gcctgtaatc ccagcacttt gggaggccga ggcgggcgga      60
tcacctgagg tcaggagttc gagaccagcc tggccaacat ggtgaaaccc cgtctctact     120
aaaaatacaa aaattagccg ggcgtggtgg cgcgcgcctg taatcccagc tactcgggag     180
gctgaggcag gagaatcgct tgaacccggg aggcggaggt tgcagtgagc cgagatcgcg     240
ccactgcact ccagcctggg cgacagagcg agactccgtc tcaaaaaaaa                290

<210> SEQ ID NO 2
<211> LENGTH: 81
<212> TYPE: DNA
<213> ORGANISM: Homo sapiens

<400> SEQUENCE: 2
gcctgtaatc ccagctactc gggaggctga ggcaggagaa tcgcttgaac ccgggaggcg      60
gaggttgcag tgagccgaga t                                                81
```

METHODS OF PREPARING A BIOFLUID SAMPLE FOR DETECTION OF KIDNEY INJURY

PRIOR RELATED APPLICATIONS

This application is a continuation of U.S. patent application Ser. No. 17/498,489, filed Oct. 11, 2021, which is a continuation of U.S. patent application Ser. No. 17/376,919, filed on Jul. 15, 2021, which is a continuation of U.S. patent application Ser. No. 16/325,385, filed on Feb. 13, 2019, which is a US National Stage application of International Patent Application No. PCT/US2017/047372, filed on Aug. 17, 2017, which claims the benefit of U.S. Provisional Application No. 62/376,299 filed on Aug. 17, 2016, each of which is incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 081906 1276045 SEQ LST.txt, created on Oct. 8, 2021, 1110 bytes, machine format IBM-PC, MS-Windows operating system, is hereby incorporated by reference in its entirety for all purposes.

BACKGROUND OF THE INVENTION

Twenty-six million Americans suffer from organ injuries, such as those associated with chronic kidney disease (CKD), and organ transplant rejection and dysfunction, e.g., kidney transplant or lung transplant. Treatment of these injuries is very costly. For example, twenty-eight percent of annual Medicare spending, $57.5 billion, is spent on treating CKD. However, for many of these, there is no way to predict when the injury is imminent until clinical symptoms emerge. A large proportion of the costs associated with these diseases are due to lack of early detection leading to more severe organ injury and requiring greater and more expensive therapeutic intervention. Methods for earlier detection of kidney pathologies would enable reductions in medical costs and more effective therapeutic intervention.

Traditionally, detection of organ injury, e.g., kidney injury, is based on examination of biopsies, which is both costly and invasive. More recently, cell-free DNA (cfDNA) from dying cells has been discovered in human urine. Recent efforts have focused on testing of urine for cfDNA as a marker for allograft rejection rather than organ injury; furthermore, the technique has been limited to using PCR or next-generation sequencing for the detection of donor-specific SNPs or the measurement of Alu elements. These methods have limitations because they are limited to testing for kidney rejection, are expensive, both in consumables and equipment, require relatively larger quantities of DNA, and are not high-throughput. Further, they may not be able to detect fragment lengths shorter than 150 bp as it has been found that, although whole, unfragmented DNA was optimal for a qPCR based approach for measuring Alu, there was a significant reduction (75% reduction) in DNA quantification for DNA at a fragment size of <150 bp (Sedlackova et al., Biol. Proced. Online (2013) 15:5. doi:10.1186/1480-9222-15-5).

BRIEF SUMMARY OF THE INVENTION

A novel methodology for quantitative analysis of cell-free DNA in biofluid, such as urine and bronchoalveolar lavage (BAL), is provided. Aspects described herein include a preservative cocktail of reagents that can stabilize biofluid cellular DNA, a method of measuring cfDNA by hybridization assay that quantifies human Alu repeats in the biofluid, and a novel analysis method that factors in clinical assay variables to provide a quantitative risk score for kidney injury. In some cases, the amounts of additional markers in the sample are measured, such as methylation markers (e.g., 5-methylcytosine), tissue inflammation markers (e.g., CXCL10), apoptosis markers (e.g., kidney tubular injury markers, such as clusterin), total protein, and/or creatinine. These aspects can be used to assess the kidney health in the context of kidney transplantation and kidney disease.

In one aspect, this disclosure provides a solution, e.g., a sterile solution, that comprises a formaldehyde donor, a chelator, aurintricarboxylic acid, and polyethylene glycol (PEG) in a concentration sufficient to inhibit cell lysis and to inhibit nucleases in urine. In some embodiments, the solution further comprises sodium azide and/or a buffer. In some embodiments, the solution further comprises a biofluidic sample. In some embodiments, the biofluidic sample is a urine sample or a BAL sample, as the effluent of choice for non-invasive measurment of kidney or lung organ injury. In some embodiments, the urine sample is from a patient who has received a kidney transplant or has acute or chronic kidney injury, in others it is the bronchoalveolar lavage (BAL) fluid from a patient who has received a lung transplant or has lung injury.

In one aspect, this disclosure provides a method of detecting Alu copy number in a biofluid sample, the method comprising: obtaining a urine or other biofluid sample from a human, extracting cfDNA from the sample, forming a reaction mixture by contacting the cfDNA with a nucleic acid probe under conditions to allow the probe to hybridize to DNA in the cfDNA that is complementary to the probe, wherein the nucleic acid probe has a nucleic acid sequence having a 3' and 5' end, wherein the nucleic acid probe is complementary to contiguous 20-292 nucleotides of SEQ ID NO:1, wherein the 3' or 5' end is covalently linked to a detectable label; and quantifying the amount of DNA hybridized to the probe. In some embodiments, the probe is complementary to at least 50 contiguous nucleotides of SEQ ID NO:2. In some embodiments, the probe comprises a sequence of 50-150, 70-100, 80-90, or exactly 81 nucleotides complementary to SEQ ID NO:1. In some embodiments, the detectable label is biotin and the method comprises contacting the detectable label with a streptavidin-linked signal producing agent.

In some embodiments, before forming the reaction mixture, mixing a solution comprising diazolidinyl urea, ethylenediaminetetraacetic acid (EDTA), aurintricarboxylic acid, and polyethylene glycol (PEG) in a concentration sufficient to inhibit cell lysis and to inhibit nucleases into the urine sample. In some embodiments, the method further comprises quantifying the amount of creatinine in the reaction mixture. In some embodiments, the method further comprises normalizing the amount of cfDNA hybridized to the probe against the amount of creatinine in the urine sample to produce a normalized amount of cfDNA. In some embodiments, the method further comprises normalizing the amount of cfDNA hybridized to the probe against the amount of creatinine in the urine sample to produce a normalized amount of hybridized DNA. In some embodiments, the method further comprises determining the patient has kidney injury if the detected amount of target DNA (e.g., cfDNA) hybridized to the probe or the normalized amount of target DNA (e.g. cfDNA) is greater than the cutoff value.

In some embodiments, the human is a patient who has received a kidney or lung transplant and the presence of kidney or lung injury indicates the patient may have acute rejection episodes. In some embodiments, the method further comprises producing a prediction score for determining kidney or lung health based on the normalized amount of target DNA (e.g., cfDNA) and the time post-transplant of the kidney. The patient is determined to have acute rejection episodes when the predictive score is greater than a cutoff value for the predictive scores. In some embodiments, the urine or BAL sample is taken 0-400 days, or 10-100 days, or 20-50 days from the patient's receiving a kidney or lung transplant.

In some embodiments, the urine sample is from an individual suspected of having a kidney injury caused by a disease selected from the group consisting of BK viral nephritis, focal segmental glomerulosclerosis (FSGS), kidney stone, acute tubular necrosis (ATN), IgA nephropathy (IgAN), and diabetic kidney disease or kidney disease from systemic diseases such as hypertension and autoimmune disorders (eg SLY, rheumatoid arthritis). In these embodiments, a determination of kidney injury indicates the patient has the disease.

In some embodiments, the method further comprises quantifying the amount CXCL10 in the reaction mixture to add greater specificity and sensitivity to the assay through the addition of a biomarker reflecting the inflammatory burden. In some embodiments, the method further comprises quantifying the proportion or absolute quantity of methylated cfDNA and hydroxymethylated cfDNA to reflect the methylation status of the circulating DNA which further defines the presence of intrinsic tissue injury.

In another aspect, the disclosure provides a reaction mixture comprising non-amplified cell-free DNA (cfDNA) extracted from a urine sample (e.g., in some embodiments, from a patient who has received a kidney transplant) and ii) a nucleic acid probe having a nucleic acid sequence and having a 3' and 5' end, wherein the nucleic acid probe is complementary to 20-292 contiguous nucleotides of SEQ ID NO:1 and wherein the 3' or 5' end is covalently linked to a detectable label. The reaction mixture can comprise any of the components described herein.

In another aspect, provided herein is a method of detecting Alu copy number in cell-free DNA (cfDNA) in a biofluid sample from an individual having a lung transplant or lung transplant clinical conditions. The method comprises obtaining a biofluid sample, e.g., a bronchoalveolar lavage (BAL) fluid sample, from a human; extracting cfDNA from the biofluidic sample; forming a reaction mixture by contacting the cfDNA with a nucleic acid probe under conditions to allow the probe to hybridize to DNA in the cfDNA that is complementary to the probe, wherein the nucleic acid probe has a nucleic acid sequence having a 3' and 5' end, wherein the nucleic acid probe is complementary to contiguous 20-292 nucleotides of SEQ ID NO:1 and wherein the 3' or 5' end is covalently linked detectable label; and quantifying the amount of DNA hybridized to the probe, thereby detecting Alu copy number in cell-free DNA (cfDNA) in the biofluidic sample. In some embodiments, the biofluidic sample is a bronchoalveolar lavage (BAL) fluid sample and wherein the method further comprises quantifying the total volume of BAL fluid.

In some embodiments, the method further comprises normalizing the amount of cfDNA hybridized to the probe against the total BAL fluid sample volume to produce a normalized amount of hybridized cfDNA.

In some embodiments, the method further comprises comparing the normalized amount of hybridized DNA to a cutoff value indicative of lung status.

In some embodiments, the method further comprises the determining the patient has lung injury if the detected amount of target DNA (e.g., cfDNA) hybridized to the probe or the normalized amount of target DNA (e.g., cfDNA) is greater than the cutoff value. In some embodiments, the human is a patient having received a lung transplant where in the lung injury indicates that patient has rejection episodes.

In some embodiments, the method further comprises generating Kidney injury Test score, a KIT score, based on the amount of cfDNA hybridized to the probe and the amount of creatinine in the reaction mixture. In some embodiments, the KIT score is generated using the ratio of the amount of DNA hybridized to the probe to the amount of creatinine. In some embodiments, the KIT score is generated by use of generalized linear models, such as logistic regression, using the amount of cfDNA hybridized to the probe, the amount of creatinine, one or more inflammation markers (e.g., CXCL10), one or more apoptosis markers (e.g., kidney tubular injury marker such as clusterin), and/or one or more DNA methylation markers present in the biofluid sample. In some embodiments, nonlinear regression models, selected from the group consisting of neural networks, generalized additive models, similarity least squares, and recursive partitioning methods, may be used to develop KIT Scores. In some embodiments, the KIT score is generated using additional biomarkers selected from the group of CXCL10, clusterin and DNA methylation markers such that the KIT score results in greater sensitivity and specificity for the diagnosis and prediction of organ injury, than the use of individual markers in the KIT assay. The KIT injury score also detects organ injury with greater sensitivity than current markers of kidney function such as the serum creatinine or urine protein or current markers of lung function, such as forced expiratory volume ("FEV") and forced vital capacity ("FVC"). In some embodiments, using the IT score, e.g., a KIT score, as described above can detect kidney injury with a sensitivity of at least 85%, at least 87%, at least 88%, at least 90%, at least 91%, at least 92%, at least 93%, at least 94%, at least 95%, and/or a specificity of at least 85%, at least 87%, at least 88%, at least 90%, at least 91%, at least 92%, at least 93%, at least 94%, at least 95%. In some embodiments, using the KIT score described above can detect kidney injury with an AUC of at least 85%, at least 87%, at least 88%, at least 90%, at least 91%, at least 92%, at least 93%, at least 94%, at least 95%, at least 96.9%, or at least 99.4%.

In some embodiments, the disclosure provides a method of detecting organ injury comprising measuring the amount of cfDNA, and amounts of one or more of markers in a biofluid sample obtained from an organ that is suspected of having injury or is likely to develop injury, wherein one or more markers is selected from the group consisting of: i) one or more inflammation markers, ii) one or more apoptosis markers, iii) total protein, and iv) one or more of DNA methylation markers; producing an IT score using the amount of cfDNA and the amounts of the one or more markers, and determining the patient having injury in the organ or predict that the patient will develop injury in the organ if the IT score is above a predetermined cutoff. In some embodiments, the organ injury is kidney injury. In some embodiments, the IT score is produced by further including creatinine. In some embodiments, the IT score is produced by using a mathematical model using the amount of cfDNA hybridized to the probe, the amount of creatinine, one or more inflammation markers (e.g., CXCL10), one or more apoptosis markers (e.g., kidney tubular injury marker such as clusterin), creatinine, and/or one or more DNA methylation markers present in the biofluid sample

BRIEF DESCRIPTION OF THE DRAWINGS

FIGS. 5A-5D show using the assay disclosed herein to distinguish kidney transplant rejection (FIGS. 5A-5B), native kidney disease (FIG. 5C) and its improved performance over proteinuria in detecting kidney injury. (FIG. 5D).

FIG. 8A shows the change of cfDNA/creatinine ratio over the days of post-transplantation and FIG. 8B shows change of the Kidney injury Test (KIT) score over the days of post-transplantation.

FIGS. 10A and 10B show using the methods disclosed herein to detect IgA nephropathy (a native kidney disease) in patients. In this study, urine samples from individuals—117 of which were healthy and 85 individuals had IgA nephropathy, as previously determined by other methods—were analyzed using the methods disclosed herein. FIG. 10A shows the differences in the detected cfDNA/creatinine ratios between healthy individuals ("normal") and those having IgA nephropathy ("IgA"). The ROC analysis indicates that the AUC of the ROC curve is 0.9651 with a confidence interval of 0.9431 to 0.9871 with a P value of <0.0001. FIG. 10B.

DETAILED DESCRIPTION OF THE INVENTION

Definitions

Figure 1A:
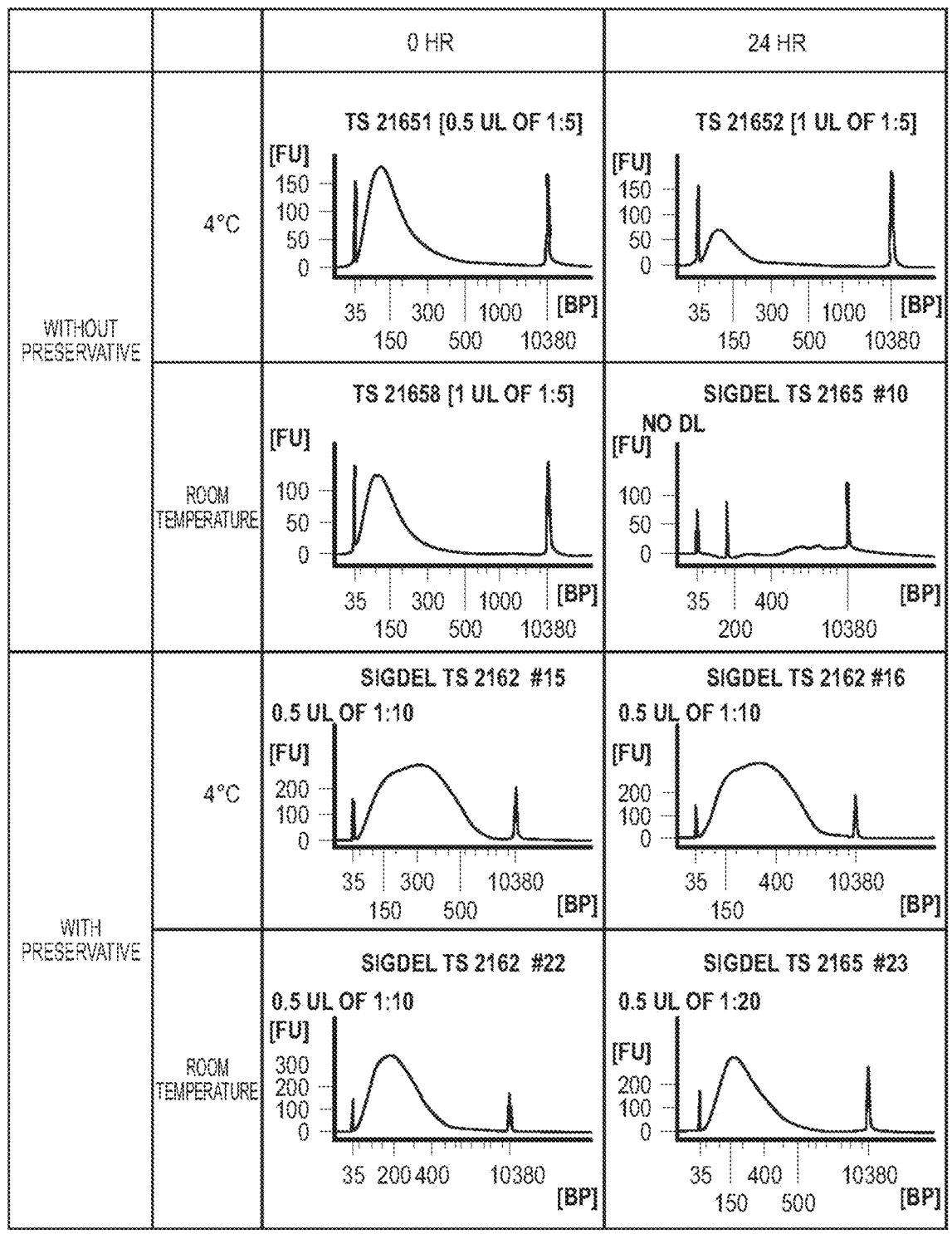
FIGS. 1A and 1B show-electropherograms that demonstrate in the absence of DNA preservative solution the DNA degrades and disintegrates completely over a period of 72 hours; whereas DNA preservation solution helps maintain DNA integrity up to 72 hours.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "subject", "patient" or "individual" are used herein interchangeably to refer to a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

The term "nucleic acid", or "polynucleotide" includes deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

The term "kidney injury status" refers to whether the patient shows injury in the kidney. For purpose of this disclosure, kidney injury can result from surgery, such as kidney transplant, or from any kidney disease.

The term "kidney transplantation" or "kidney transplant" refers to the organ transplant of a kidney into a patient. The source of the donor kidney can be from a deceased or living donor.

The term "Alu" or "Alu element" or "Alu repeat" refers to a short stretch, about 300 base pairs long, of DNA originally characterized by the action of the *Arthrobacter luteus* restriction endonuclease. Alu elements are the most abundant repetitive elements in the human genome. They are derived from the small cytoplasmic 7SL RNA. SEQ ID NO:1 represents an exemplary human Alu repeat.

The term "hybridize" refers to the annealing of one or more probes to a target nucleotide sequence. Hybridization conditions typically include a temperature that is below the melting temperature of the probes but that avoids nonspecific hybridization of the probes.

The term "biofluid" or "biofluidic sample" refers to a fluidic composition that is obtained or derived from an individual that is to be characterized and/or identified, for example based on physical, biochemical, chemical and/or physiological characteristics. Non-limiting examples of biofluid include blood, serum, plasma, saliva, phlegm, gastric juices, semen, tears, and sweat. In one embodiment the biofluid is urine. In another embodiment the biofluid is BAL.

The term "post-transplantation" refers to a time after the transplantation of an organ, e.g., kidney or lung, into the patient from a donor.

As used herein, the term "AUC" refers to "area under the curve" or C-statistic, which is examined within the scope of ROC (receiver-operating characteristic) curve analysis. AUC is an indicator that allows representation of the sensitivity and specificity of a test, assay, or method over the entire range of test (or assay) cut points with just a single value. An AUC of an assay is determined from a diagram in which the sensitivity of the assay on the ordinate is plotted against 1-specificity on the abscissa. A higher AUC indicates a higher accuracy of the test; an AUC value of 1 means that all samples have been assigned correctly (specificity and sensitivity of 1), an AUC value of 50% means that the samples have been assigned with guesswork probability and the parameter thus has no significance.

Using AUCs through the ROC curve analysis to evaluate the accuracy of a diagnostic or prognostic test are well known in the art, for example, as described in, Pepe et al., "Limitations of the Odds Ratio in Gauging the Performance of a Diagnostic, Prognostic, or Screening Marker," Am. J. Epidemiol 2004, 159 (9): 882-890, and "ROC Curve Analysis: An Example Showing The Relationships Among Serum Lipid And Apolipoprotein levels In Identifying Subjects With Coronary Artery Disease," Clin. Chem., 1992, 38(8): 1425-1428. See also, CLSI Document EP24-A2: Assessment of the Diagnostic Accuracy of Laboratory Tests Using Receiver Operating Characteristic Curves; Approved Guideline—Second Edition. Clinical and Laboratory Standards Institute; 2011; CLSI Document PLA21-A2: Clinical Evaluation of Immunoassays; Approved Guideline—Second Edition. Clinical and Laboratory Standards Institute; 2008.

As used herein, the term "diagnose" means assigning symptoms or phenomena to a disease or injury. For the purpose of this invention, diagnosis means determining the presence of organ injury in a subject.

As used herein, the term "predict" refers to predicting as to whether organ injury is likely to develop in a subject.

1. Kidney Injury Status

Compositions and methods are provided that can be used to assess kidney injury status, i.e., the presence or absence of kidney injury in an individual. Such an assessment is helpful for diagnosing when an individual is in need of medical intervention, such as being given more medication to address the medical problem or having medication decreased (including cessation) where it is no longer medically necessary. For example, compositions and methods described herein can be used to determine when an individual has kidney injury due to kidney transplant or kidney disease.

Kidney injury can develop in patients who have undergone a kidney transplant. This can happen because of several immune and non-immune factors such as ischemia reperfusion injury, size disparity, donor related factors, cell-mediated rejection, and antibody-mediated rejection, by way of example. Problems after a transplant may include: transplant rejection (hyperacute, acute or chronic), infections and sepsis due to the immunosuppressant drugs that are required to decrease risk of rejection, post-transplant lymphoproliferative disorder (a form of lymphoma due to the immune suppressants), imbalances in electrolytes including calcium and phosphate which can lead to bone problems among other things, and other side effects of medications including gastrointestinal inflammation and ulceration of the stomach and esophagus, hirsutism (excessive hair growth in a male-pattern distribution), hair loss, obesity, acne, diabetes mellitus type 2, hypercholesterolemia, and osteoporosis.

Kidney injury can also develop in patients having kidney disease. Kidney diseases are diverse, but individuals with kidney disease frequently display characteristic clinical features. Common clinical conditions involving the kidney include but are not limited to the nephritic and nephrotic syndromes, renal cysts, acute kidney injury, chronic kidney disease, diabetes-induced nephropathy, urinary tract infection, nephrolithiasis, and urinary tract obstruction, glomerular nephritis (GN), focal segmental glomerular sclerosis (FSGS), IgA nephropathy (IgAN), mesangiocapillary, lupus and membranous etc, hypertensive nephropathy, and drug induced nephropathy. Kidney diseases can also include the various cancers of the kidney which exist. For example such cancers include, but are not limited to, renal cell carcinoma, urothelial cell carcinoma of the renal pelvis, squamous cell carcinoma, juxtaglomerular cell tumor (reninoma), angiomyolipoma, renal oncocytoma, bellini duct carcinoma, clear-cell sarcoma of the kidney, mesoblastic nephroma, Wilms' tumor, mixed epithelial stromal tumors, clear cell adenocarcinoma, transitional cell carcinoma, inverted papilloma, renal lymphoma, teratoma, carcinosarcoma, and carcinoid tumor of the renal pelvis. Kidney disease can also be virally induced and include, but are not limited to BKV nephropathy and nephropathy induced by EBV and CMV. Kidney disease can also be drug-induced as some medications are nephrotoxic (they have an elevated risk for harming the kidneys). In the worst case, the drug causes kidney failure, while in other cases, the kidneys are damaged, but do not fail. Common nephrotoxic drugs include, but are not limited to, nonsteroidal anti-inflammatory drugs (NSAIDs), some antibiotics, some painkillers, and radiocontrast dyes used for some imaging procedures.

In some embodiments, a urine sample is from an individual having a kidney transplant, or one of the above-listed kidney disorders or kidney transplant clinical conditions described above is assayed as described herein.

2. Lung Injury Status

Compositions and methods are provided herein that can be used to assess lung injury status, i.e., the presence or absence of lung injury in an individual. Such an assessment is helpful for diagnosing when an individual is in need of medical intervention, such as being given more medication to address the medical problem or having medication decreased (including cessation) where it is no longer medically necessary. For example, the compositions and methods described herein can be used to determine when an individual has lung injury due to lung transplant.

Lung injury can develop in patients who have undergone a lung transplant. This can happen because of several immune and non-immune factors such as ischemia reperfusion injury, size disparity, donor-related factors, cell-mediated rejection, and antibody-mediated rejection, by way of example. Problems after lung transplantation may include hyperacute rejection, acute rejection, several types of chronic rejection or chronic lung allograft dysfunction (CLAD) such as restrictive allograft syndrome (RAS) or bronchiolitis obliterans syndrome (BOS), infections, and sepsis due to the immunosuppressant drugs that are required to decrease risk of rejection.

In some embodiments, a biofluid sample, e.g., a bronchoalveolar lavage (BAL) fluid sample, is from an individual having a lung transplant, or lung transplant clinical conditions described above is assayed as described herein. Thus, in some embodiments, provided herein is a method of detecting Alu copy number in cell-free DNA (cfDNA) in a biofluid sample from an individual having a lung transplant or lung transplant clinical conditions. The method comprises obtaining a biofluid sample, e.g., a bronchoalveolar lavage (BAL) fluid sample, from a human; extracting cfDNA from the biofluidic sample; forming a reaction mixture by contacting the cfDNA with a nucleic acid probe under conditions to allow the probe to hybridize to DNA in the cfDNA that is complementary to the probe, wherein the nucleic acid probe has a nucleic acid sequence having a 3' and 5' end, wherein the nucleic acid probe is complementary to contiguous 20-292 nucleotides of SEQ ID NO:1 and wherein the 3' or 5' end is covalently linked detectable label; and quantifying the amount of DNA hybridized to the probe, thereby detecting Alu copy number in cell-free DNA (cfDNA) in the biofluidic sample The amount of DNA hybridized to the probe may be normalized against the total biofluid sample volume to produce a normalized amount of hybridized DNA. In some cases, the normalized amount of hybridized DNA is compared to a cutoff value indicative of lung status. In some cases, the method further comprises determining the patient has lung injury if the detected amount of target DNA (e.g., cfDNA) hybridized to the probe or the normalized amount of target DNA (e.g., cfDNA) is greater than the cutoff value.

3. The Preservation Cocktail

In some aspects, a preservative cocktail of reagents that can stabilize biofluid cell-free DNA ("cfDNA") is provided. In some embodiments, the preservative cocktail is a solution comprising a formaldehyde donor and a chelator, such as a calcium chelating agent. Non-limiting examples of formaldehyde donor include diazolidinyl urea and imidazolidinyl urea. Non-limiting examples of chelators include EDTA and EGTA. In some embodiments, the solution further comprises one or both of PEG, aurintricarboxylic acid. In some embodiments, the solution further comprises sodium azide, and a buffer. Non-limiting examples of buffers include PBS, TAPS, Bicine, Tris, Tricine, HEPES, TES, MOPS, PIPES, Cacodylate, and MES. In some embodiments, the solution comprises the respective components at a concentration that can preserve the biofluid (e.g., urine) by preventing degradation of cfDNA by nucleases, and/or by inhibiting cell lysis. In addition to stabilizing cfDNA, the solution can also prevent genomic DNA contamination through stabilization of cells present in the biofluid. Various molecular weight of PEG and various forms of EDTA can be used in this cocktail to provide the desired properties above. In one embodiment, the PEG used in the cocktail is PEG 35,000. In one embodiment, EDTA is Na2EDTA. In one embodiment, EDTA is K2EDTA. In one embodiment, EDTA is K3EDTA.

Typically, the cocktail is prepared as a concentrated stock solution, e.g., a 100×, 20×, 10×, 5×, or 2× concentrated stock solution, and is mixed and diluted with biofluid to be assayed, e.g., a urine sample, to a final working concentration. For example, for a 10× concentration of the cocktail, which will be diluted 10 times after mixing with urine, the concentration of diazolidinyl urea can be 0.1 g/L to 50 g/L, e.g., 0.5 g/L to 30 g/L, 1 g/L to 20 g/L, 5 g/L to 20 g/L, 5 g/L to 15 g/L, or 5 g/L to 10 g/L; the concentration of PEG 35,0000 can be 0.2 g/L to 50 g/L, e.g., 0.5 g/L to 40 g/L, 1 g/L to 30 g/L, 20 g/L, or 15 g/L to 25 g/L; the concentration of aurintricarboxylic acid can be 0.1 mM to 10 mM, e.g., 0.0.2 mM to 10 mM, 0.0.5 mM to 5 mM, 0.5 mM to 2 mM, or 1 mM to 2 mM. The concentration of EDTA can be 1 mM to 100 mM, e.g., 2 mM to 50 m, 5 mM to 40 mM, 5 mM to 20 mM, or 10 mM to 20 mM. The 10× concentrated stock solution may also comprise sodium azide at a concentration of 1 mM to 100 mM, 2 mM to 50 mM, 5 mM to 20 mM, or 10 mM to 15 mM. The cocktail can comprise a buffer, such as phosphate buffer saline (PBS), for example 10×PBS in a 10× concentrated stock solution.

In some cases, the cocktail is provided in a powder or solid table format and is reconstituted to solution by adding water or aqueous buffer, or the biofluid itself.

In certain embodiments, the cocktail comprises about 10 g/L Diazolidinyl Urea, about 20 g/L PolyEthelyene Glycocol, about 1 mM Aurintricarboxylic acid, about 10 mM K2EDTA, about 10 mM Sodium Azide, and/or about 1× Phosphate Buffered Saline, pH7.4.

4. The Nucleic Acid Probe

The Alu gene has been extensively studied for amplification of various regions for assessing the quantity of cfDNA in patients with cancer (*Biol Proced Online* (2013); Park et al., Oncol Lett (2012)). In one aspect, the present invention provides a method of assessing the quantity of cfDNA in biofluids by using a labeled nucleic acid probe to hybridize to the Alu repeats in cfDNA.

In some embodiments, the nucleic acid probe comprises a nucleotide sequence that comprises, or is fully complementary to, at least 20-300, e.g., 20-292, 20-180, 50-150, 70-100, 80-90 contiguous nucleotides of SEQ ID NO: 1:

5' GGCCGGGCGCGGTGGCTCACGCCTGTAATCCCAGCACTTTGGGAGGC

CGAGGCGGGCGGATCACCTGAGGTCAGGAGTTCGAGACCAGCCTGGCCA

ACATGGTGAAACCCCGTCTCTACTAAAAATACAAAAATTAGCCGGGCGT

GGTGGCGCGCGCCTGTAATCCCAGCTACTCGGGAGGCTGAGGCAGGAGA

ATCGCTTGAACCCGGGAGGCGGAGGTTGCAGTGAGCCGAGATCGCGCCA

CTGCACTCCAGCCTGGGCGACAGAGCGAGACTCCGTCTCAAAAAAAA-

3'.

In some embodiments, the probe comprises a nucleotide sequence that comprises, or is fully complementary to, at least 20, 30, 40, 50, 60, 70, 80, or 81 contiguous nucleotides of SEQ ID NO: 2:

GCCTGTAATCCCAGCTACTCGGGAGGCTGAGGCAGGAGAATCGCTTGAA
CCCGGGAGGCGGAGGTTGCAGTGAGCCGAGAT.

A nucleotide referred to herein in the context of the nucleic acid probe can be a natural nucleotide, e.g., cytosine, guanine, thymine, adenosine, or a modified nucleotide. A modified nucleotide refers to an alteration in which at least one nucleotide of the oligonucleotide sequence is replaced by a different nucleotide that provides a desired property (e.g., ability to base pair with a complementary nucleotide in a target nucleic acid) to the oligonucleotide. Non-limiting examples of modified nucleotide include locked nucleic acids (LNA), peptide nucleic acids (PNA), morpholinos, and those described in US Pat. Pub. No. 20160177377.

In some embodiments, the nucleotide sequence of the probe is conjugated to a detectable label. The detectable label can be conjugated onto any nucleotide of the probe so long as it does not inhibit hybridization of the probe to the target, i.e., the Alu repeats in the cfDNA. In some embodiments, the 5' end of the nucleotide sequence is conjugated to one or more (e.g., two or more) detectable label. In some embodiments, the detectable label itself is conjugated to the signal-producing agent. In some embodiments, the detectable label is a molecule that can bind a binding partner and the binding partner is linked to a signal producing agent. For example, in some embodiments, the detectable label is biotin and the binding partner is streptavidin or vice versa. In some embodiments the detectable label is digoxigenin and its binding partner is anti-digoxigenin or vice versa. In some embodiments, the detectable label is 2, 4-dinitrophenol (DNP) and the binding partner is anti-DNP or vice versa. Other labels known to one skilled in the art can also be used in the nucleic acid probe disclosed herein. The signal—producing agent can be any agent that produces quantifiable signal, including but not limited to, chemiluminescence, color, or fluorescence. Non-limiting examples of signal-producing agents include an enzyme, a fluorescent molecule, or the like. Other non-limiting examples of detectable labels and signal-producing agents can be found in US20130209990, hereby incorporated by reference. In one preferred embodiment, the signal-producing agent is horseradish peroxidase (HRP).

In some cases, the 3' end of the nucleotide sequence of the probe is conjugated to one or more detectable label. In some cases, both the 5' and 3' ends of the nucleotide sequence are conjugated to one or more detectable label. The number of detectable labels conjugated to the probe can vary, for example, the number can be at least one, two, three, four, five, six, seven, ten, fifteen, eighteen, or more. In general, a higher number of detectable labels will produce a higher signal in the assay (Division et al., Nucleic Acids Res. (1988) 16: 4077-4095). One of ordinary skill can readily determine the number of detectable labels to be used based on the amount of signal required to detect the target, e.g., the Alu repeats, in the cell-free DNA from biofluid.

In one embodiment, the 5' or the 3' end of the nucleic acid sequence of the probe is conjugated to one biotin. In one embodiment the total number of biotin conjugated to the nucleic acid sequence is 1, or 18, or any number in between. The one or more biotin can be all conjugated at the same 5' or 3' end of the nucleic acid probe. The one or more biotin can also be conjugated at both ends, in any combination. In some embodiments, two biotins are conjugated to the nucleic acid sequence of the probe. In one embodiment, the two biotins are conjugated to the 5' end of the nucleic acid sequence of the probe.

The nucleic acid probes described herein may be produced by any suitable method 3 known in the art, including for example, by chemical synthesis, isolation from a naturally-occurring source, recombinant production and asymmetric PCR (McCabe, 1990 In: PCR Protocols: A guide to methods and applications. San Diego, Calif., Academic Press, 76-83). It may be preferred to chemically synthesize the probes in one or more segments and subsequently link the segments. Several chemical synthesis methods are described by Narang et al. (1979 Meth. Enzymol. 68:90), Brown et al. (1979 Meth. Enzymol. 68:109) and Caruthers et al. (1985 Meth. Enzymol. 154:287), which are incorporated herein by reference. Alternatively, cloning methods may provide a convenient nucleic acid fragment which can be isolated for use as a promoter primer. A double-stranded DNA probe can be first rendered single-stranded using, for example, conventional denaturation methods prior to hybridization to the target in cfDNA in biofluids.

5. Method of Use

In some embodiments, the methods involve linking cfDNA (not previously amplified) to a solid support, hybridizing a probe specific for an Alu repeat to the cfDNA, removing (e.g., washing away) unbound probe, and then detecting the amount of specifically hybridizing probe, thereby determining the amount of cfDNA in a sample.

a. Obtaining Biofluid Samples

Biofluid samples, e.g., urine or BAL, from individuals, e.g., those suspected of having organ injury, can be collected in any manner recommended by a medical professional, e.g., being collected, mid-stream, in sterile containers. In some embodiments, the sample is then processed through centrifugation to remove cellular components, thereby producing a cell-free sample. Optionally, the sample can be mixed with a buffer (e.g., PBS or Tris) and/or the above-described preservation cocktail. The sample can be stored at −80° C. until further analysis. In some embodiments, a preservative cocktail as described above is added to the biofluid sample to produce a mixture. In some embodiments, the mixture can be aliquoted for extraction of cfDNA.

b. Extracting Cell Free DNA

Methods for extracting cell free DNA are well known in the art and commercial kits are readily available, for example, QIAamp® Circulating Nucleic Acids Kit from Qiagen (Valencia, Calif.). In general, the sample can be treated to degrade cell debris and remove DNase and RNase to produce a lysate. DNA in the lysate can be extracted by e.g., passing the lysate through a DNA binding column and the bound DNA can be eluted with water or buffer. Optionally, an aliquot of the eluent can be taken to determine the concentration of the cfDNA recovered.

The cfDNA is subsequently linked to a solid support. Solid supports can be a containing vessel, a bead or any other solid support. In some embodiments, the cfDNA is placed in a desired vessel, for example, in the wells of a microwell plate and incubated for a period of time that is sufficient to allow the cfDNA to bind surface of the wells. In some embodiments, the incubation occurs over a period of at least one, at least two, at least four hours long, optionally at room temperature. In some embodiments, the incubation occurs at 4° C. for at least 8 hours. After the incubation, the vessel can be washed and blocked with a blocking solution, e.g., a solution comprising 5% BSA to minimize non-specific binding. The blocking solution can comprise a buffer (e.g., PBS). The blocking solution can then be removed before adding the nucleic acid probe for hybridizing with the target, i.e., the Alu repeats.

c. Hybridizing a Nucleic Acid Probe with Alu Repeats

Hybridization assays of the nucleic acid probe with the Alu repeats in cfDNA can be performed in any reaction vessel, including but not limited to a multi-well plate, e.g., a 96-well plate, e.g., the 96-well LUMITRAC 600 (Greiner Bio-One). The assay of detecting cfDNA using a hybridization assay, i.e., hybridization of a probe conjugated to a detectable label without previous amplification of the target nucleic acid is desirable compared to a PCR-based approach because hybridization assays are cost-effective and can be multiplexed to a higher grade (e.g., 384/batch). In addition, the hybridization approach allows for more complete and accurate quantification of cfDNA as the probe will detect all single and double-stranded cfDNA in the biofluid, irrespective of fragment length.

In an exemplary hybridization assay, a pre-determined volume of cfDNA extracted from the biofluids as described above is allowed to bind to a support, e.g., the bottom of the microplate wells. In some embodiments, the surface of the support is previously treated to increase the binding affinity of the cfDNA to the surface of the reaction vessel. In some embodiments, a buffer (e.g., PBS) and salts (e.g., $MgCl_2$) is added to facilitate hybridization between the probe and cfDNA. The final working concentration of the salt can be 0.05M-0.5M, e.g., 0.05M-0.2M, or 0.1M. Optionally, a standard curve can be created using known quantities of human DNA extract.

Hybridization of the cfDNA and the nucleic acid probe can be conducted under standard hybridization conditions. Reaction conditions for hybridization of a probe to a nucleic acid sequence vary from probe to probe, depending on factors such as probe length, the number of G and C nucleotides in the sequence, and the composition of the buffer utilized in the hybridization reaction. Moderately stringent hybridization conditions are generally understood by those skilled in the art as conditions approximately 20° C.-50° C., e.g, 25° C.-40° C. below the melting temperature of a perfectly base-paired double stranded DNA. Higher specificity is generally achieved by employing incubation conditions having higher temperatures, in other words more stringent conditions. Chapter 11 of the well-known laboratory manual of Sambrook at al., MOLECULAR CLONING: A LABORATORY MANUAL, second edition, Cold Spring Harbor Laboratory Press, New York (1990) (which is incorporated by reference herein), describes hybridization conditions for oligonucleotide probes in great detail, including a description of the factors involved and the level of stringency necessary to guarantee hybridization with specificity. Hybridization is typically performed in a buffered aqueous solution, for which conditions such as temperature, salt concentration, and pH are selected to provide sufficient stringency such that the probes hybridize specifically to their respective target nucleic acid sequences but not any other sequence.

Generally, the efficiency of hybridization between the nucleic acid probe and target, e.g., the Alu repeats in cfDNA, improves under conditions where the amount of probe added is in molar excess to the template. In some embodiments, the nucleic acid probe of the invention is diluted in 5% BSA at a concentration of between 10 ng/µl-200 ng/µl, e.g., 20 ng/µl-100 ng/µl, 30 ng/µl-75 ng/µl, 30 ng/µl-50 ng/µl. In a particular embodiment, nucleic acid probe is the double-biotinylated and is used at the concentration of 30-40 ng/µl. The nucleic acid probe and the cfDNA in the plate can be incubated to allow the hybridization of the probe and the Alu repeats in the cfDNA. The wells of the plate can then be washed (e.g., with PBS or another buffer) and optionally dried before detection.

d. Detecting Signal

Methods of detecting signal produced by detectable labels are well-known in the art and the methods vary depend on the nature of the chemical reaction employed to produce the signal. As described above, in some embodiments, the detectable label itself is a signal producing agent that produce a signal, which can be read directly using appropriate equipment, for example, a plate reader. In some embodiments, the detectable label produces signal indirectly, a solution comprising a binding partner of the label that is conjugated to a signal producing agent is added to the plate to produce the signal. The signal producing agent include, for example, enzyme or enzyme substrates, reactive groups, chromophores such as dyes or colored particles, luminescent moieties including a bioluminescent, phosphorescent or chemiluminescent moieties, and fluorescent moieties. In one embodiment, the detectable label is biotin and the binding partner is streptavidin and the signal producing agent is horse radish peroxidase (HRP). In this particular embodiment, the signal is a chemiluminescent signal, which can be readily detected and quantified by methods well known in the art.

e. Detecting Creatinine Levels

The quantification of cfDNA disclosed herein can be combined with measurement of a urine protein. In one specific embodiment the urine protein is creatinine. Creatinine can be measured using the Jaffe reaction, an absorbance based method. Commercial assays for measuring creatinine are readily available, such as the QuantiChrom™ Creatinine Assay Kit (BioAssay Systems), which produces an output in mg of creatinine/deciliter of urine. See, e.g., www.bioassay-sys.com/Datasheet/DICT.pdf. In some embodiments, urine creatinine measurements are taken before or after extracting and quantifying cfDNA in the urine sample. In some embodiments, urine creatinine measurements and cfDNA quantification are performed in the same microwell plate (but different wells), by e.g., placing urine samples for measuring creatinine in the same microplate as the cfDNAs extracted from these urine samples. Measuring the creatinine and cfDNA in the same plate/assay saves time and cost as compared to conventional PCR methods, which requires one assay to read the amount of amplification product of the cfDNA and one assay to read creatinine level.

f. Detecting Additional Markers.

Additional known markers can be measured to further improve the sensitivity and/or specificity of detection of organ injury. In some embodiments, the additional markers comprise one or more tissue inflammatory markers, e.g., CXCL10. e.g., inflammation in the kidney. In some embodiments, CXCL10 is detected and quantified. Methods for measuring CXCL10 is well known, for example, using a sandwich ELISA approach, where a capture antibody adsorbs onto the plate first and then sample is added to allow the CXCL10 in the sample to be captured. Afterwards, a detection antibody is added that will bind the captured CXCL10. This can be detected using the usual secondary antibody—HRP conjugation approaches well known in the literature. A standard curve would be generated with standard concentrations of purified CXCL10 protein. Commercial kits are readily available for measuring CXCL10, for example, Human CXCL10/IP-10 Quantikine ELISA Kit from R & D systems. Urine CXCL10 can be measured before or after the cfDNA measurement. Urine CXCL10 can also be measured in the same microwell plate as cfDNA, by e.g., coating CXCL10 capture antibody in designated wells in the microplate first and placing urine samples for measuring CXCL10 in these designated wells.

In addition, differential methylation status of the cfDNA in urine adds additional significance for kidney injury and markers correlated with methylation status can be measured and added to the assay described above for detecting kidney injury. Thus, in some embodiments, the additional markers comprise one or more DNA methylation markers. In one particular embodiment, the DNA methylation marker is 5-emthylcytosine that is incorporated into the nucleic acid in the sample.

DNA methylation markers can be detected and quantified using an ELISA-based approach. Commercial kits that are used to measure the DNA methylation markers are readily available, for example, the MethylFlash Urine 5-Methylcytosine (5-mC) Quantification Kit from EpiGentek that is used to measure the amount of 5-methylcytosine incorporated in the DNA. Briefly, a plate that has methylated DNA is incubated with the sample and an antibody that recognize the methylation marker. This solution is allowed to incubate and is then washed and further detected with a detection antibody and/or substrate.

In some embodiments, the additional markers comprise total protein in the biofluid sample. The amount of total protein can be measured using any methods known in the art that can be used to measure the protein. In one embodiment, the assay to measure total protein is a colorimetric assay, e.g., the Bradford protein assay.

In some embodiments, the additional markers comprise clusterin. Clusterin is a protein that is associated with the clearance of cellular debris and apoptosis. The presence of clusterin can also be detected and measured using a ELISA-based assay. such as the Human Clusterin DuoSet ELISA. Like other sandwich ELISAs, a plate with capture antibody against Clusterin bound to it is incubated with urine samples, optionally diluted in sample diluent. A detection antibody also against Clusterin is then incubated with the plate, and an HRP-detection system is used to measure absorbance.

g. Optional Reagents and Devices.

The methods may be used in a variety of assay devices and/or format. The assay devices may include, e.g., assay plates, cartridges, multi-well assay plates, reaction vessels, test tubes, cuvettes, flow cells, assay chips, lateral flow devices, etc., having assay reagents (which may include targeting agents or other binding reagents) added as the assay progresses or preloaded in the wells, chambers, or assay regions of the assay module. These devices may employ a variety of assay formats for specific binding assays, e.g., immunoassay or immunochromatographic assays. Illustrative assay devices, e.g., microwell plates and formats, 96-well plate format, are described herein below.

In certain embodiments, the methods can employ assay reagents that are stored in a dry state and the assay devices/kits may further comprise or be supplied with desiccant materials for maintaining the assay reagents in a dry state. The assay devices preloaded with the assay reagents can greatly improve the speed and reduce the complexity of assay measurements while maintaining excellent stability during storage. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports.

In some embodiments, the methods described above can be performed in a lateral flow assay ("LFA"). LFA depends on the capillary action of a fluid sample drawn across a pad that contains capture reagents to the antigen of interest. In some embodiments, the biofluid sample is mixed upon application to a device, e.g., a dipstick or a test strip, with reagents that are either purified antigen of interest bound to a visible marker (e.g. colloidal gold) in a competitive format or an antibody that is bound to a visible marker and recognize an antigen of interest in the biofluid sample in a non-competitive format. The antigen of interest can be any molecule in the biofluid sample, for example, any of the markers disclosed in this application, such as creatinine, cfDNA, methylation markers, CXCL10, and/or clusterin. In some embodiments, a competitive format of LFA is used to measure the creatinine and/or methylation markers. In some embodiments, a non-competitive format LFA is used to measure cfDNA, CXCL10, and/or clusterin.

6. Determination of Organ Injury Status a. Determining Organ Health Based on the Amount of cfDNA In some embodiments, the determination organ health of an individual comprises comparing the amount of cfDNA in the biofluid sample to a cutoff value or predictive probability estimate indicative of organ injury status. The cutoff value can be a pre-determined value or predictive probability estimate, e.g., a value recommended by medical professionals. Depending on circumstances, it may be necessary in some cases to establish a cutoff value for the determination. To establish such a cutoff value for practicing methods disclosed herein, a group of healthy individuals, such as a group of individuals who do not have organ injury after a organ transplantation is selected. These individuals are within the appropriate parameters, if applicable, for the purpose of determining organ injury status using the methods of the present invention. For instance, the individuals may be of similar age, gender, and comparable health status.

In some embodiments, to assess kidney injury, the detected amount of cfDNA, i.e., the amount of DNA hybridized to the nucleic acid probe, in urine is first normalized to the amount of urine creatinine to produce a normalized amount of cfDNA. In some cases, the normalized amount of cfDNA is a ratio of the detected amount of cfDNA to the amount of creatinine in urine. To determine the kidney injury status, the normalized amount of cfDNA is compared to a cutoff value, which is also a relative ratio of the cfDNA amount to the creatinine amount in urine, as determined to be indicative of kidney injury status by medical professionals or established as described above.

If the amount of cfDNA or the normalized amount of cfDNA in urine is higher than its respective cutoff value, the patient is determined to have kidney injury; in general, a higher value indicates a higher degree of kidney injury. In some cases, if the amount of cfDNA or normalized amount of cfDNA is higher than but near the cutoff value, the patient is determined to have subclinical injury. If the amount of cfDNA or the normalized amount of cfDNA in urine is equal to or lower than its respective cutoff value, the patient is determined to have no kidney injury, i.e., good kidney health. For patients who have received kidney transplants, detection of kidney injury from urine indicates they are likely to have acute rejection episodes. For patients who are suspected of having certain kidney disease, in some embodiments, detection of kidney injury indicates the patients are likely to have the kidney disease.

Figure 6:
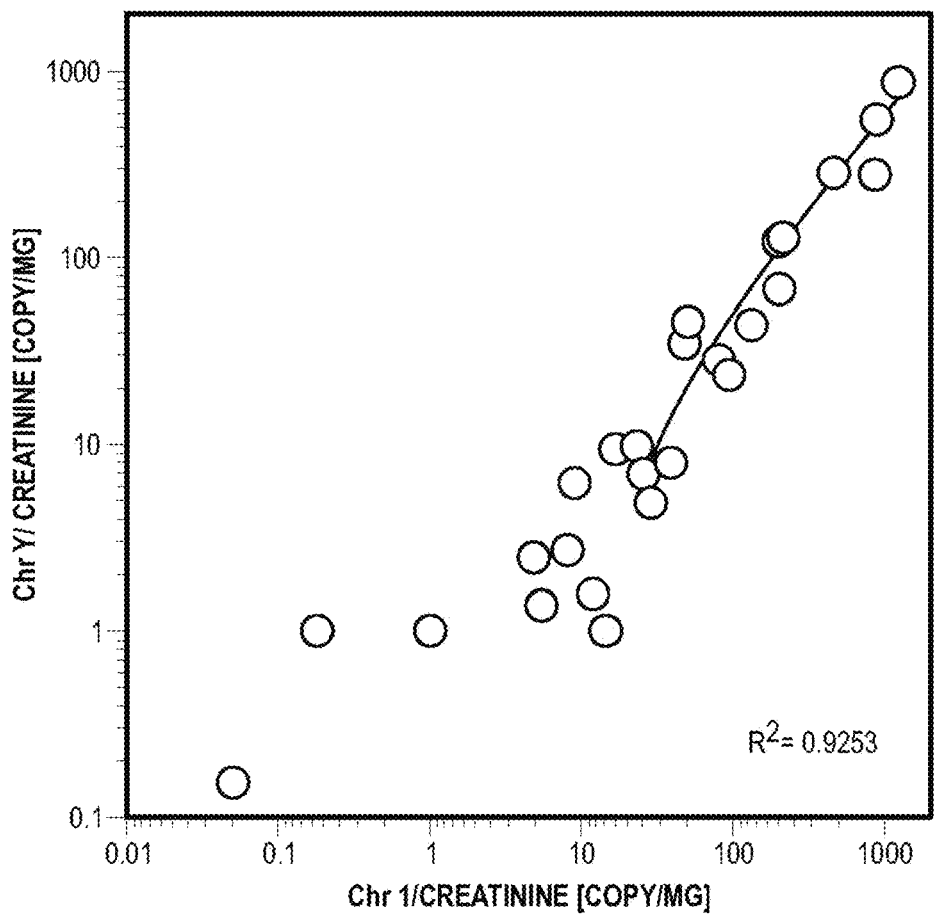
FIG. 6 shows the correlation between chromosome Y and chromosome 1 copy number in the urine validates the method in this disclosure.

In contrast to conventional methods of detecting cfDNA in the blood, which would be contaminated with cfDNA mostly from the recipient of the kidney transplant, cfDNA detected in the urine specifically reflects donor-derived DNA, even when testing for total cfDNA. FIG. 6 shows the correlation between chromosome Y and chromosome 1 copy number in the urine. The strong linear correlation ($R^2=0.9253$) indicates quantification of total cfDNA reflects the donor-derived burden and correctly reflects the kidney injury status due to the kidney transplantation.

b. Determining Organ Injury Status for Organ Transplantation Patients Using a IT Score In certain embodiments, a predictive score, i.e., IT score, is used to diagnose whether a patient who has received an organ transplant may have organ injury, or to predict the likelihood a patient will develop organ injury in the future. Organ injury developed after organ transplant is typically associated with acute rejection episodes to the transplanted organ.

The IT score can be a composite value that can be calculated based on the amount of cfDNA in a biofluid sample from the organ and a factor ('normalizing factor") that can be used to normalize the amount of cfDNA in the biofluid sample. In one embodiment, the amount of creatinine is used to normalize the cfDNA in urine. In another embodiment, the sample volume of the BAL is used to normalize the cfDNA in BAL from lung. The IT score may also include the time point, i.e., days post-transplantation, when the biofluid sample is taken. The time post-transplant can be a confounder of organ injury because patients often experience injuries that are not necessarily due to the rejection to the transplanted organ, for example, the ongoing nephrotoxic injury to the transplanted organ from ischemia reperfusion and nephrotoxic damage due to infections and calcineurin inhibitor drug exposure. These injuries are not indicative of acute rejection and the extent of such injuries may vary at different time points post transplantation. Thus, the IT score, taking the time includes time point post transplantation, can accurately predict whether the patient has acute rejection episodes to the transplanted organ.

Figure 12:
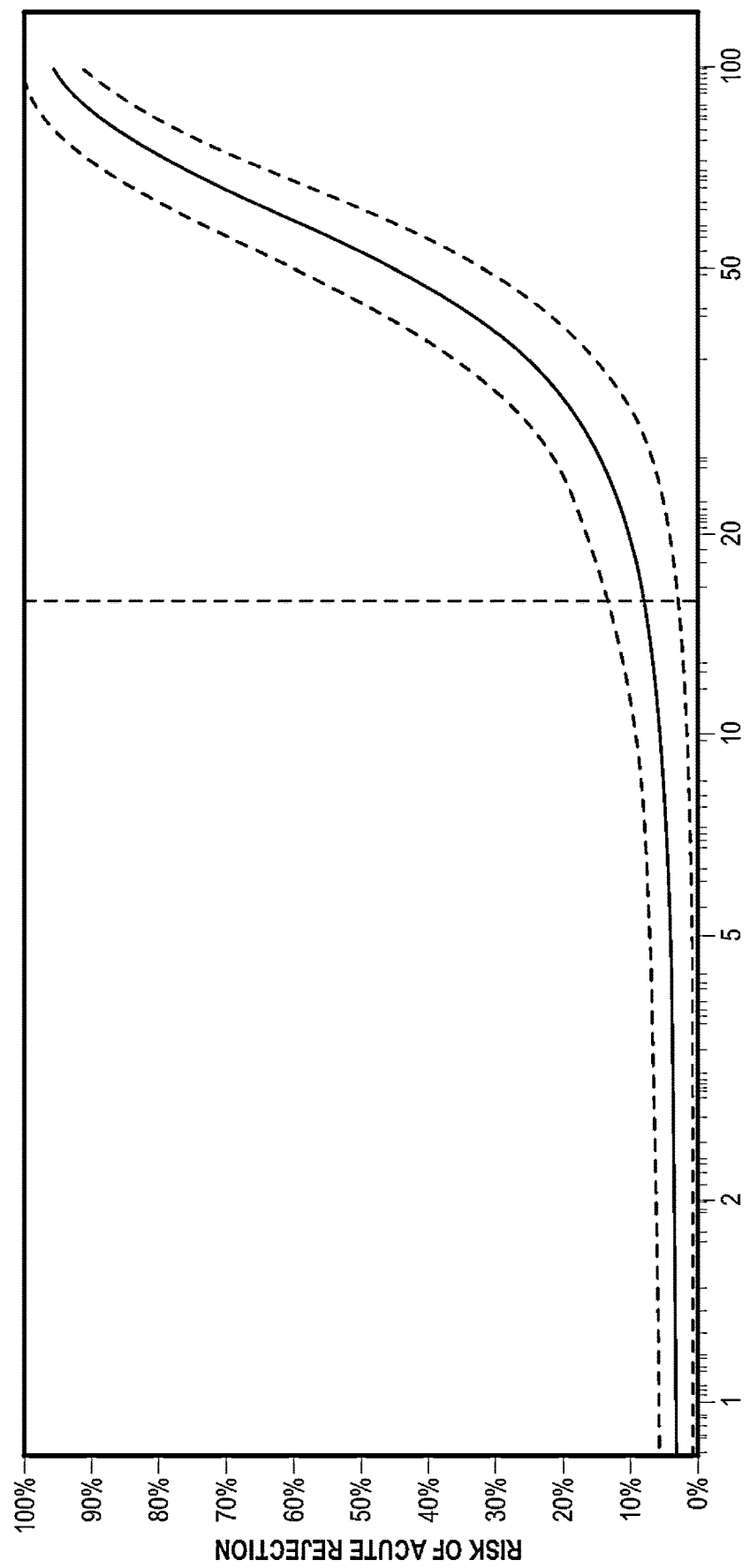
FIG. 12 shows a predictiveness curve for the probability of acute kidney rejection in kidney transplant patients as a function of a KIT score, which is generated using measurements of cfDNA and creatinine from urine. Urine samples from 41 patients having received kidney transplants were collected as disclosed herein. Measurements of cfDNA and creatinine in urine were obtained from each patient.

In some embodiments, measurements of cfDNA in the biofluid sample may be combined with other biomarkers in the biofluid sample to form the IT score that can be used to diagnose and/or predict organ injury. In some embodiments, multivariate methods can be used to incorporate these other biomarkers, e.g., to CXCL10 and DNA methylation markers, to calculate the IT score. In some embodiments, cfDNA concentrations are normalized relative to the amount of creatinine in the sample by taking the ratio of cfDNA to creatinine or scaling the logarithmic measurements of cfDNA and creatinine proportionately (e.g. through regression analysis). In some embodiments, cfDNA concentrations are normalized relative to the sample volume of BAL by taking the ratio of cfDNA to the volume or scaling the logarithmic measurements of cfDNA and volume proportionately (e.g. through regression analysis). In some cases, the generated values are regressed using generalized linear models incorporating a quasibinomial distribution and a logistic link function. In some cases, the resulting model probability estimates for acute rejection are rescaled from 0-100 to form the IT score and used to generate predictiveness curve. FIG. 12 shows an illustrative embodiment, which displays the probability of acute kidney rejection in kidney transplant patients as a function of the resulting a IT score for assessing kidney injury ("KIT").

Figure 13:
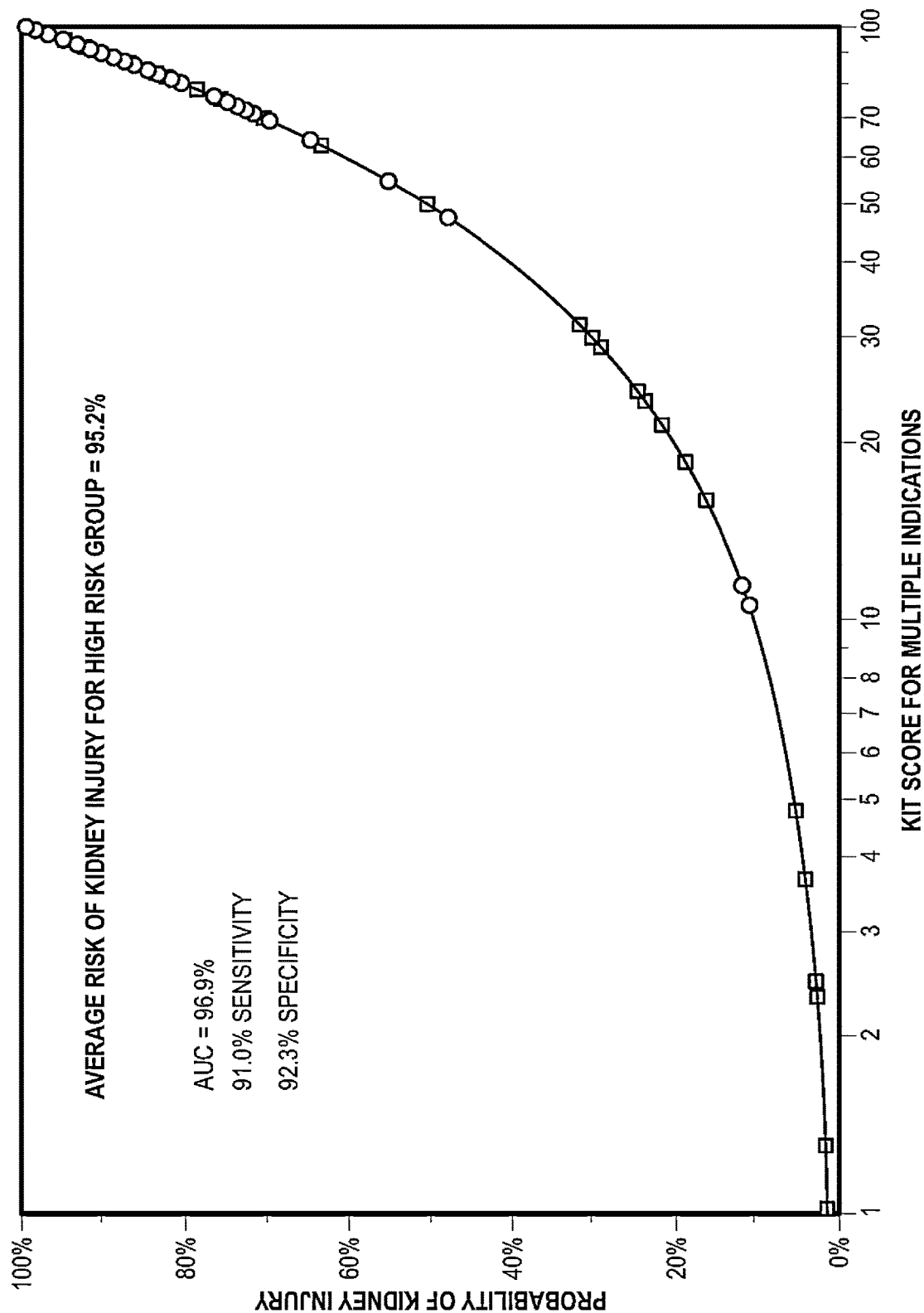
FIG. 13 shows using a KIT score to assess kidney injury based on a dataset of 490 clinical samples with multiple causes of kidney injury.
Figure 14A:
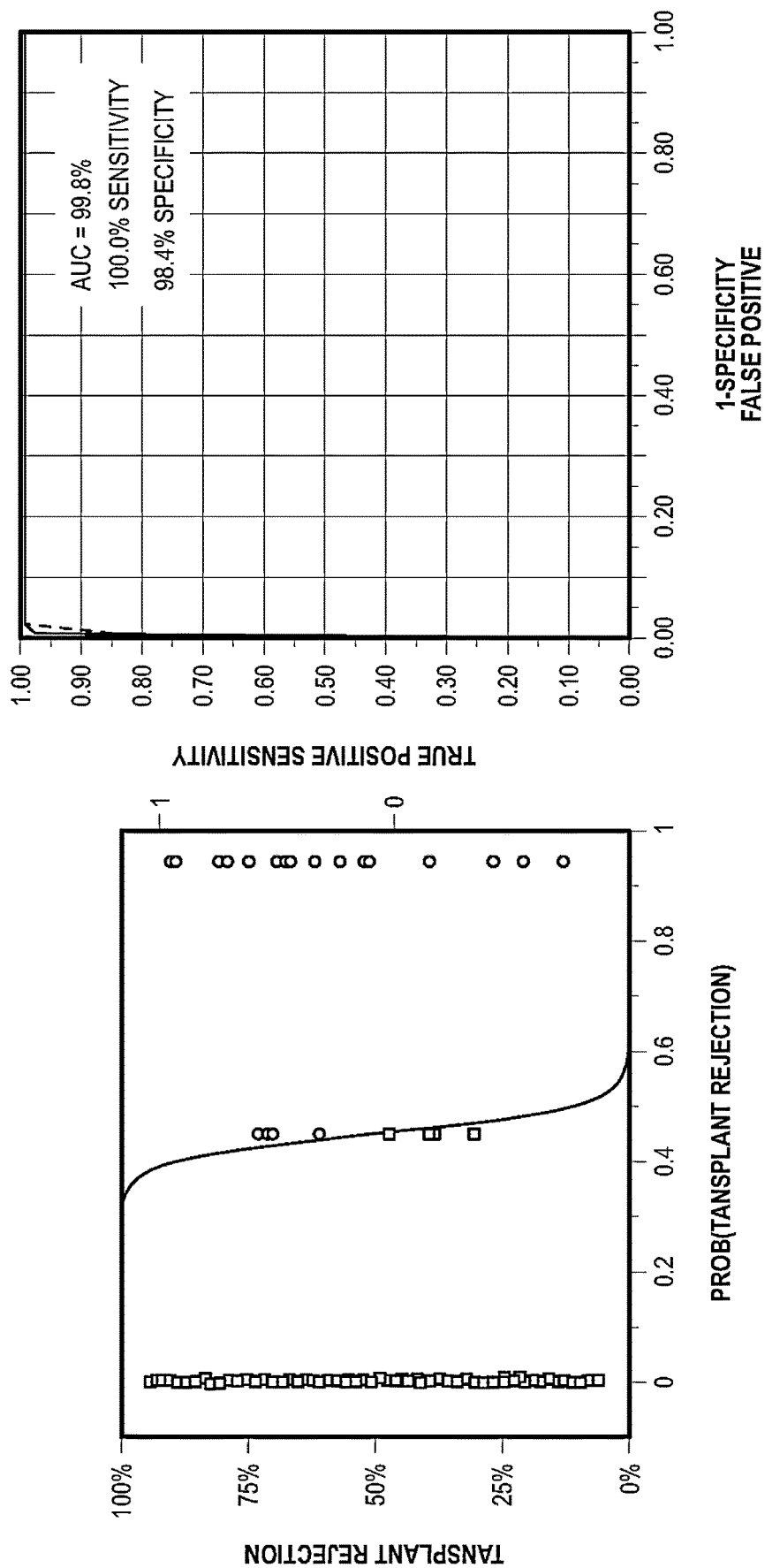
FIGS. 14A-14E show using generalized linear model and associated ROC curves to predict probability of kidney injury as well as various diseases that are associated with kidney injury, namely, type II diabetes mellitus, immune response, kidney stones, transplant rejection, and hypertension.
Figure 14B:
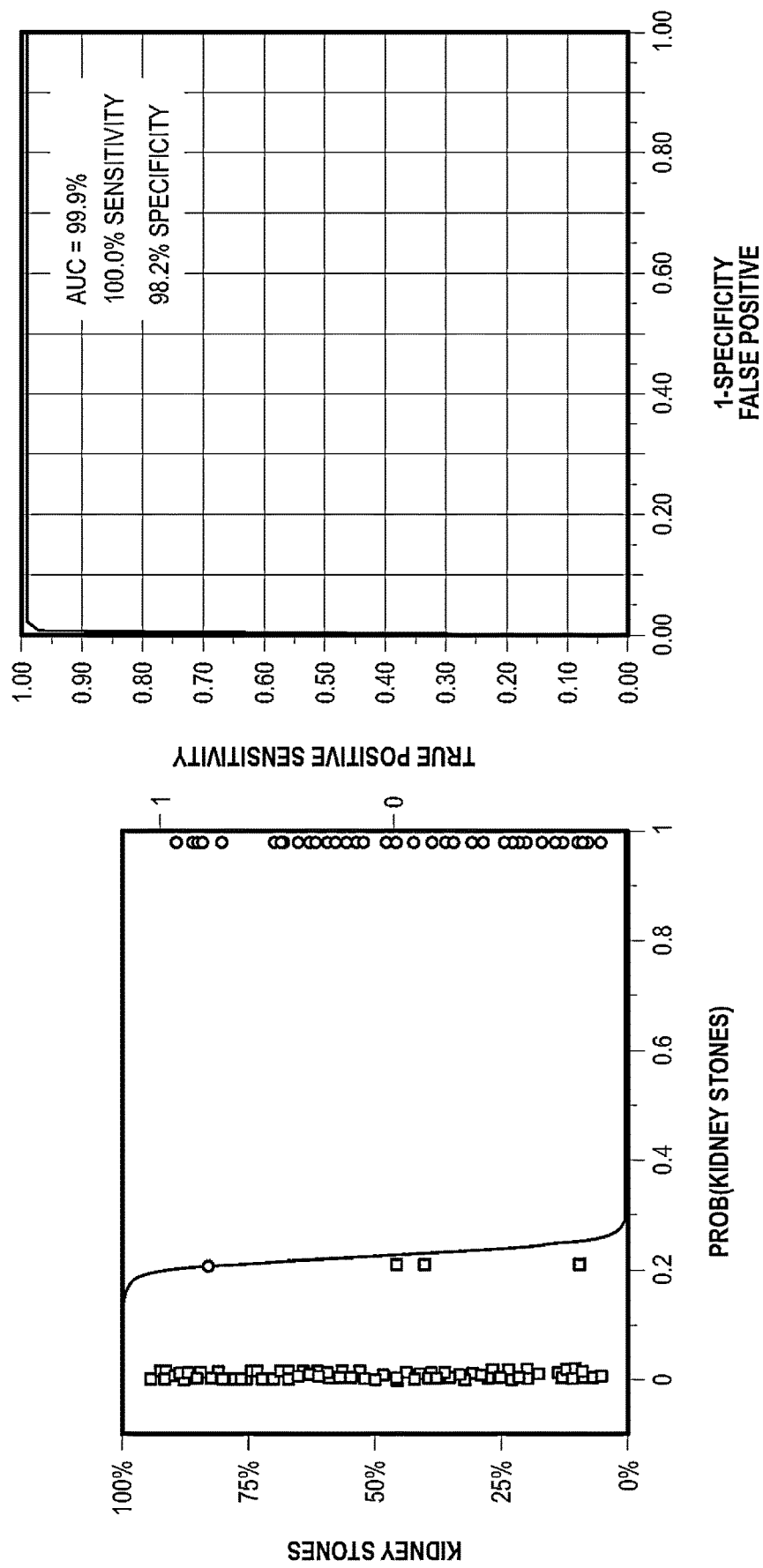
Figure 14C:
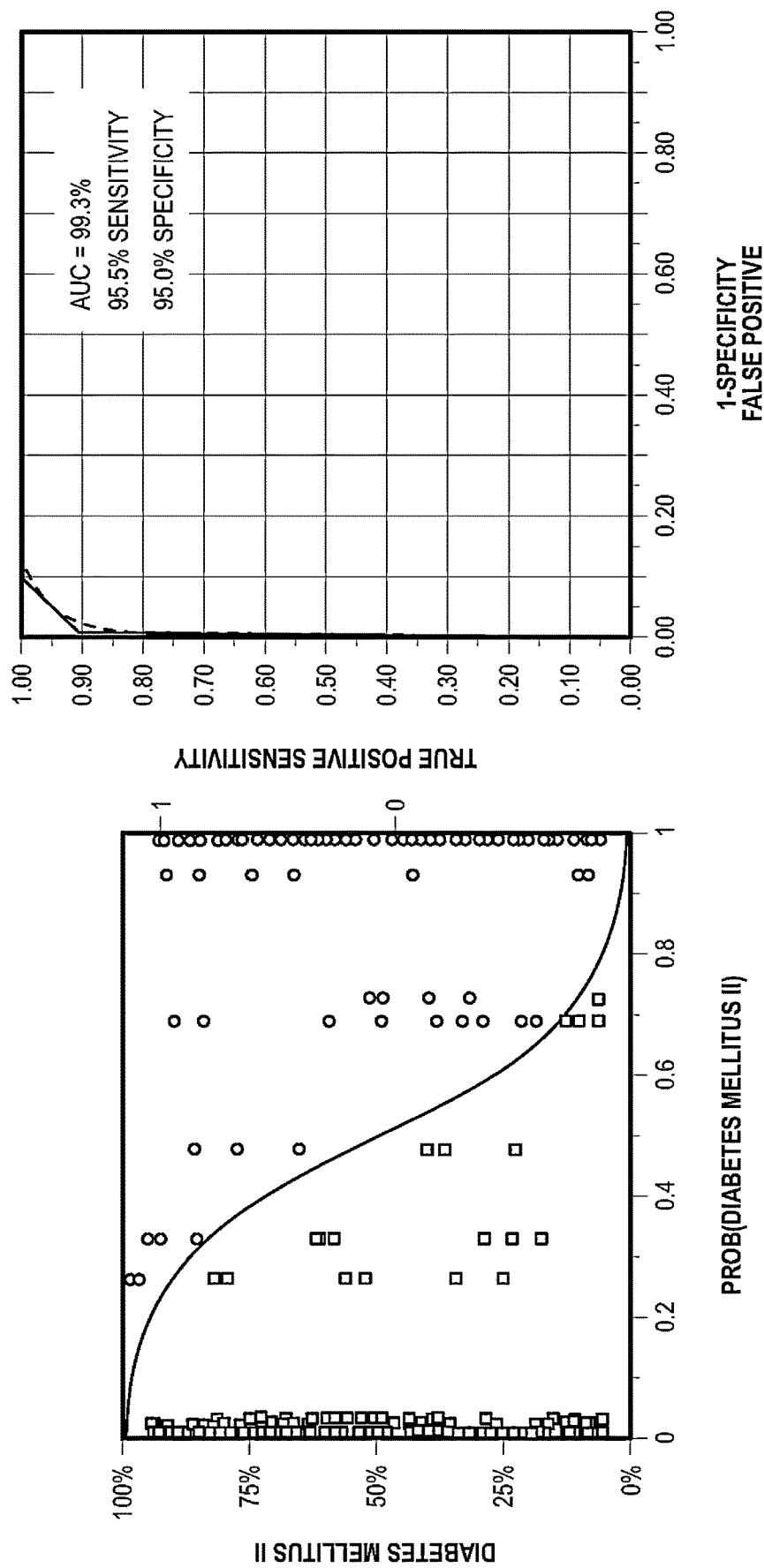
Figure 14D:
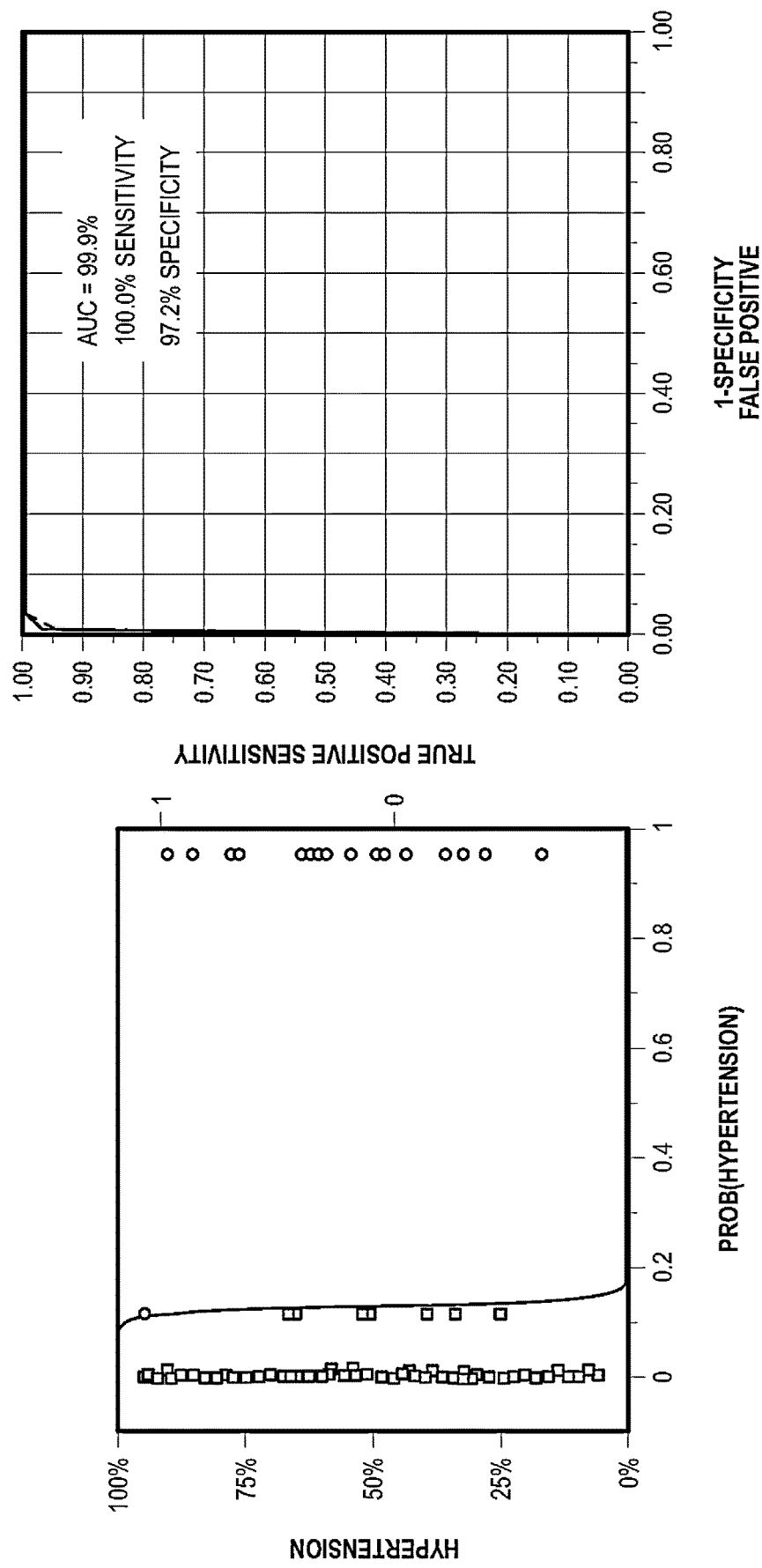
Figure 14E:
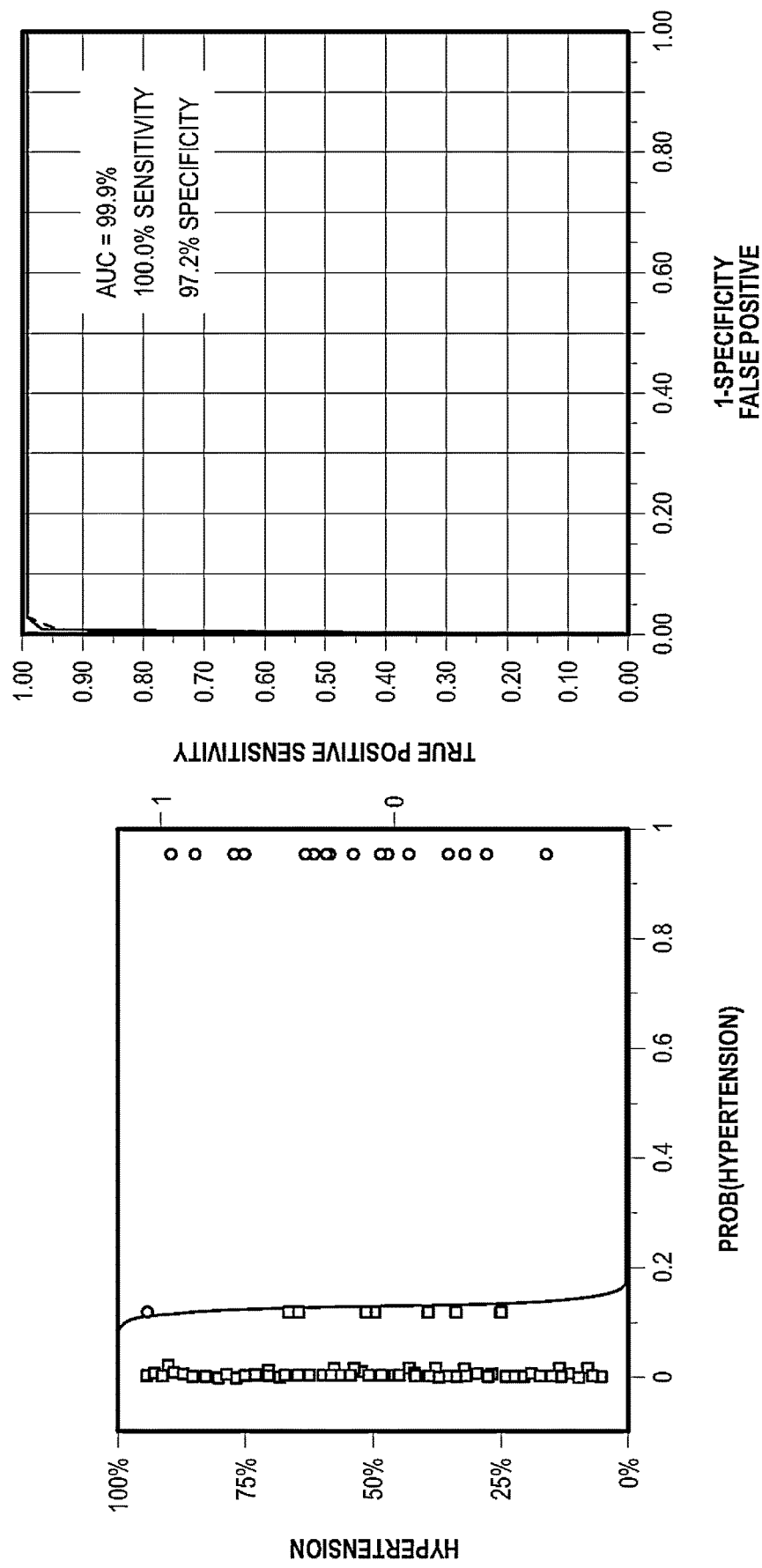

In some embodiments, an IT score, e.g., a KIT score, can be used to predict or diagnose organ injury with high specificity and sensitivity. In some embodiments, the IT score is generated by including the amount of cfDNA, the amount of DNA methylation markers, and/or inflammation markers present in the biofluid sample from the organ that is suspected of having injury or being likely to develop injury in the future. In some embodiments, the IT score is a KIT score for assessing kidney injury. In some embodiments, the KIT score is generated by further including the amount of creatinine and/or the amount of a kidney tubular injury marker (e.g., clusterin). In some embodiments, the IT score produced by including multiple markers as described above can detect organ injury with a sensitivity of at least 85%, at least 87%, at least 88%, at least 90%, at least 91%, at least 92%, at least 93%, at least 94%, at least 95%, and/or a specificity of at least at least 85%, at least 87%, at least 88%, at least 90%, at least 91%, at least 92%, at least 93%, at least 94%, at least 95%. In some embodiments, using the KIT score described above can detect kidney injury with a AUC of at least 85%, at least 87%, at least 88%, at least 90%, at least 91%, at least 92%, at least 93%, at least 94%, at least 95%, at least 96.9%, or at least 99.4%. FIG. 13 provides an illustrative embodiment, which displays a IT score for assessing kidney injury ("KIT") based on a dataset of 490 clinical patient samples with multiple causes of kidney injury. The resulting KIT score is based on a subset of 299 clinical patient samples that had complete measurements of cfDNA, creatine, CXCL10, Clusterin, Protein, and DNA methylation markers; 111 type II diabetes mellitus, 71 immune, 50 kidney stones, 20 transplant rejections, 19 hypertension and 28 controls. The resulting KIT score has over 91% sensitivity and specificity for detection of kidney injury (AUC=96.9%).

In some embodiments, mathematical models/algorithms are used to develop the IT scores using the amount of cfDNA and one or more markers as described above. Such models may include generalized linear models, such as logistic regression; and nonlinear regression models, such as neural networks, generalized additive models, similarity least squares, and recursive partitioning methods. In some embodiments, the mathematical models/algorithms that are used to generate the IT score are executed by one or more computer processors. Preferably, the mathematical models used to develop the IT scores are based on a database comprising sufficient sample size. In some embodiments, the database comprises at least 50, at least 60, at least 70, at least 100, at least 200, at least 300, or at least 400 samples. FIGS. 14a-14e provide an illustrative embodiment of using generalized linear model fits and associated ROC curves to provide the probability of kidney injury, as well as the probability of kidney injury due to each disease cause; namely, type II diabetes mellitus, immune response, kidney stones, transplant rejection, and hypertension. In one specific embodiment as shown in FIGS. 14A-E, the resulting algorithm has over 92% sensitivity and specificity (AUC>99.4%) for detection of each cause of kidney injury.

In some embodiments, a cutoff value for the IT scores can be established by measuring markers present in biofluid samples from the same or similar types of organs from a group of healthy individuals, such as a group of individuals who do not have organ injury after an organ transplantation is selected. These individuals are within the appropriate parameters, if applicable, for the purpose of determining organ injury status using the methods of the present invention. For instance, the individuals may be of similar age, gender, and comparable health status. The cutoff value of the IT scores is then produced using mathematical models and/or markers that are the same as those used to generate the IT scores for patients to be tested.

In some embodiments, multivariate methods have been used to incorporate multiple biomarkers, e.g., to CXCL10 and DNA methylation markers, with cfDNA and creatinine to further refine the KIT score and the KIT score can be used to diagnose and/or predict kidney injury that has been induced by multiple clinical conditions such as diabetes I, diabetes II, kidney stones, cancer, and immune complexes such as IgA nephropathy.

A number of ways can be used to produce the KIT score. In some embodiments, a cutoff value of the cfDNA/creatinine ratios is first determined based on normalized cfDNA values (e.g., normalized to creatinine levels) from urine samples from kidney transplant patients who have not shown rejection. These urine samples can be collected at predetermined time points over a post-transplantation period. KIT scores for a patient can then be determined based on the patient's normalized cfDNA values. Such normalized values can then be compared to cutoff values for those time points to determine whether the normalized values are predictive of healthy or diseased kidney function. Such comparisons can be performed on a computer if desired.

In some embodiments, the cutoff value is the cfDNA/creatinine ratios in patients who received kidney transplantation but who have not shown organ injury at respective time points in a post-transplantation period. In some embodiments, a prediction band of normalized cfDNA levels can be generated and a patient's actual normalized cfDNA value can be compared to the value in the prediction band corresponding to the same time point post-transplantation. The prediction band can be established in a variety of ways. In some embodiments, a number of stable, non-rejecting patients were examined over time and an exponential decay curve was fit to the cfDNA/creatinine values with respect to time post-transplant. The prediction band was subsequently generated based on a prescribed probability to cover the values of future observations from the same group that was sampled. For example, a 95% prediction band consists of upper limits of cfDNA/creatinine ratios from 95% of stable non-rejecting patients examined at various time points post-transplantation. The KIT score at a particular time post-transplantation is then determined based on the actual measurements of cfDNA/creatinine and the prediction band value corresponding to that time point.

In some approaches, the cfDNA values relative to the creatinine values are processed into other forms of information, e.g., by using either common mathematical transformations, e.g., by using logarithmic transforms, or statistical models, such as logistic or generalized linear models. Other data processing approaches, such as normalization of the results in reference to a population's mean values, etc. are also well known to those skilled in the art and can be used.

The KIT score is typically a numerical score on a defined scale or within a defined range of values. The KIT score can be compared with a cutoff value of the KIT scores that is predictive of whether the patient has acute rejection episodes. If the KIT score is above the cutoff value of the KIT scores, a patient is predicted to have kidney injury, indicating he or she is likely to have acute rejection (AR) episodes. In some cases, a higher KIT score indicates a higher degree of injury due to the AR episodes. For example, in the case where the KIT score is the logarithm of the patent's cfDNA/creatinine ratio divided by the cutoff value of the ratio, the cutoff value of the KIT score is 0.

Figure 5D:
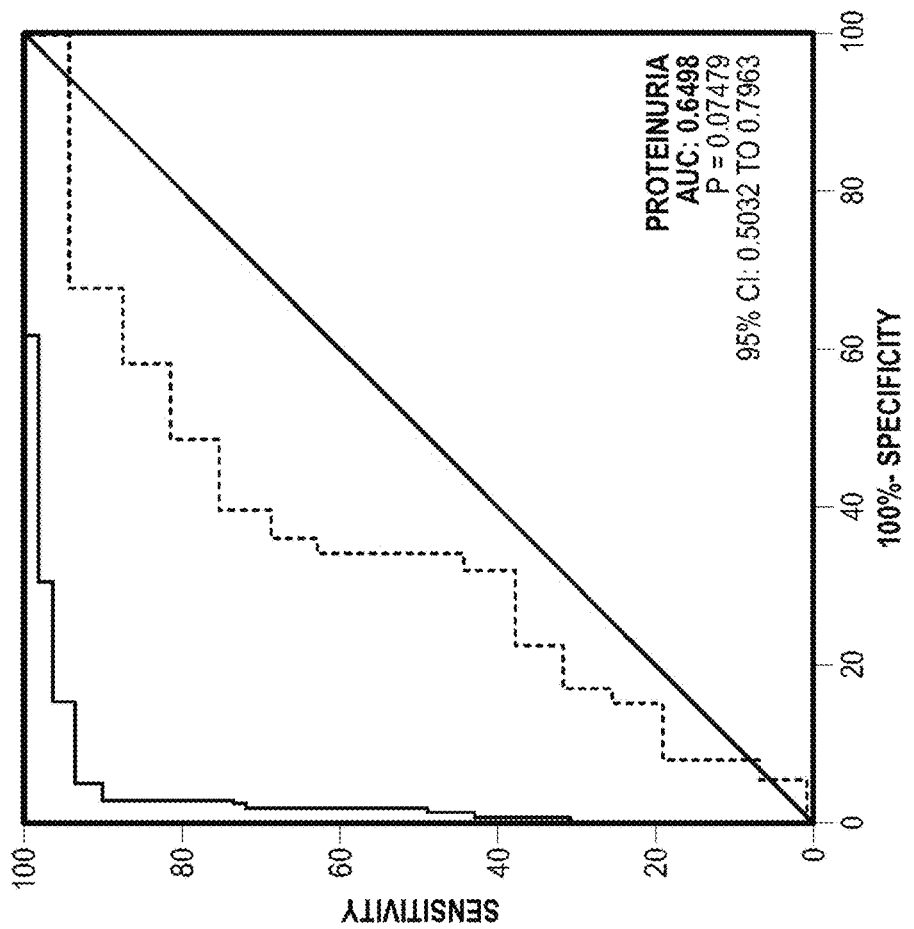
Figure 5C:
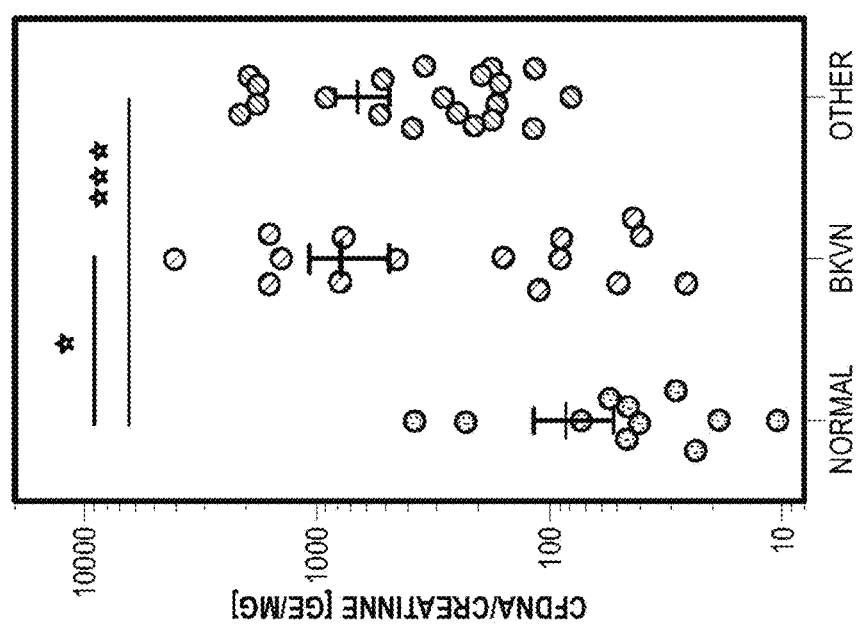

The KIT score is highly predictive of organ injuries associated with acute rejection and can be used to determine if the patient has acute rejection episodes. See FIG. 5A. Receiver operating characteristic curves (ROC) analysis of showed that AUC of ROC curve for detecting acute rejection using the KIT score was 0.9649, with a p-value of 0.0001 and a 95% confidence interval of 0.9346-0.9952, indicating the method is highly sensitive and specific FIG. 5B. In contrast, the conventional kidney injury prediction method, i.e., detecting proteinuria, had a much lower AUC of 0.6498, with a p-value of 0.07479 and a confidence interval of 0.5032-0.7963. The significance of difference was tested using McNemar's Paired chi-square from results from the same set of patients. The p-value was 0.021, suggesting that KIT is providing information above and beyond protein and that they are significantly different with respective to sensitivity. This comparison suggests that KIT method is more acute than the proteinuria method in determining acute rejection McNemar Test results:

| | KIT & Protein | |
| --- | --- | --- |
| | | Protein |
| KIT | .00 | 1.00 |
| .00 | 34 | 20 |
| 1.00 | 7 | 17 |

| Test Statistics[a] | |
| --- | --- |
| | KIT & Protein |
| N | 78 |
| Chi-Square[b] | 5.333 |
| Asymp. Sig. | .021 |

[a]McNemar Test
[b]Continuity Corrected

In some embodiments, the KIT score is generated by further including measurements of other known kidney injury markers, in addition to the cfDNA/creatinine ratios, at various time point post-transplantation increase assay sensitivity. These markers include but not limited to CXCL10 and DNA methylation markers, as described above. For any biomarker of interest, a longitudinal trend curve can be generated for each of these biomarkers and an exponential decay curve i.e. a 90% or 95% predication band, can be established in a manner similar to what is used to generate the prediction band for the cfDNA/creatinine ratios.

Approaches similar to what is disclosed above, i.e., methods of generating a KIT score and using the generated KIT score to assess kidney injury, can be used to produce KIT scores to assess injury of any other organ, e.g., injury developed after an organ transplant.

Thus, the present invention can be used to conveniently monitor organ transplant patients for organ injuries associated with acute rejection episodes by either using the cfDNA normalized amounts (e.g., normalized to creatinine levels) or the IT scores corresponding to designated time points over a period of time post-transplantation. The period can be of any length as deemed necessary by the treating physician, e.g., at least 20 days, at least 50 days, at least 100 days, at least 150 days, at least 200 days, or at least 400 days, at least 500 days, or the life time of the transplanted kidney. Measuring cfDNA and creatinine can be performed at any frequency as deemed necessary, e.g., at least once year, at least twice a year, at least every three months, at least every two months, or at least every one month, or at least every 20 days, or at least every 10 days. Patients who are so determined to have acute rejection episode can be treated as soon as possible, for example, by administering immunosuppressant drugs. Non-limiting examples of immunosuppressant drugs include calcineurin inhibitors, such as Tacrolimus and Cyclosporine; anti-proliferative agents, such as Mycophenolate Mofetil, Mycophenolate Sodium and Azathioprine; mTOR inhibitors, such as Sirolimus, steroids such as Prednisone, and induction agents such as thymoglobulin, IL2R blockade or belatacept. On the other hand, if the IT score is equal to or below the cutoff value, the patient is determined to have no kidney injury and thus no intervention is needed. If a patient has a IT score near the cutoff value, the patient is determined to have subclinical injury. The IT scores can assist the treating physicians to determine whether the kidney transplantation was successful and whether and when intervention is needed. In addition, a patient specific trend of the IT score can also be analyzed to determine whether any clinical intervention is needed. For example, a trend of increase in the IT scores suggests that the patient is developing acute rejection episodes and therefore the clinical intervention may be necessary.

c. Detecting Kidney Diseases

Figure 4:
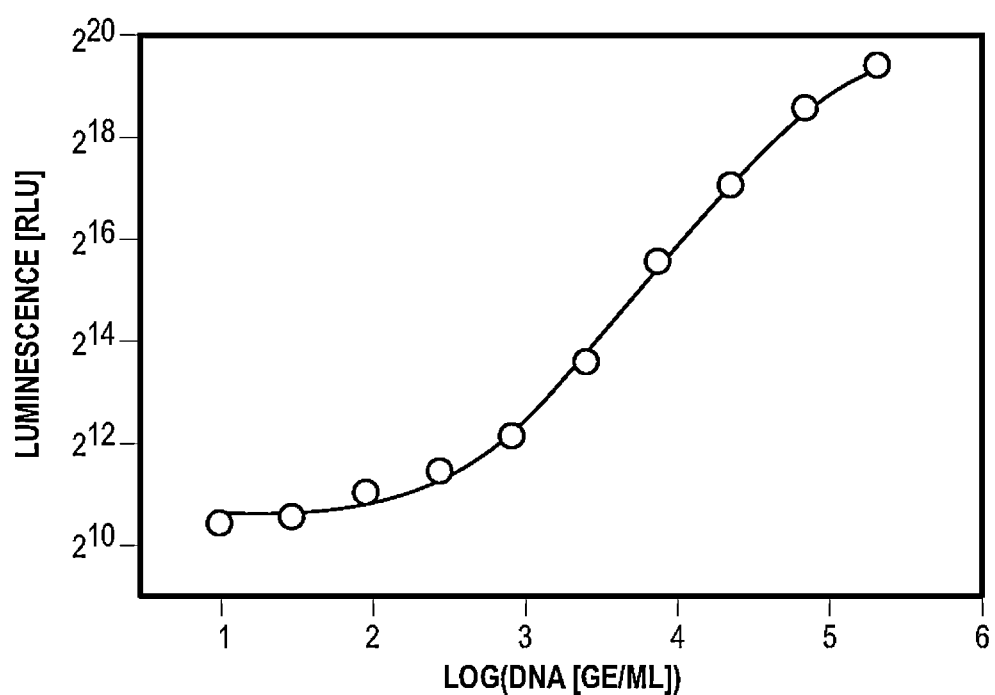
FIG. 4. shows the dynamic range of the assay disclosed herein having at least 5 orders of magnitude using a chemiluminescent assay system.

In the cases of kidney injury associated with kidney diseases, the KIT score is not applicable, and the determination is based on the cfDNA/creatinine ratio as described above. In some cases, the addition of other biomarkers, e.g., CXCL10 that can be multiplexed onto the cfDNA plate may be applicable in creating a predictive model for the detection. The methods can be used to detect kidney diseases such as focal segmental glomerulosclerosis (FSGS), IgA nephropathy, and early diabetic kidney disease, BK viral nephritis (BKVN), focal segmental glomerulosclerosis (FSGS), glomerulonephritis (GN), acute tubular necrosis (ATN), IgA disease and diabetic kidney disease. FIG. 4C shows the use of cfDNA/creatinine ratio to separate patients having BKVN from those not having the disease.

d. Computer and Smart Phone Devices

In some embodiments, signals from the one or more markers described herein, e.g., cfDNA, creatinine, e.g., as detected from a lateral flow assay, are transmitted to a computer device, a camera, or a smart phone. In some embodiments, the signals are tranmitted to a smart phone app for processing.

EXAMPLES

Example 1. The Probe Targeting the Alu Element

Figure 2:
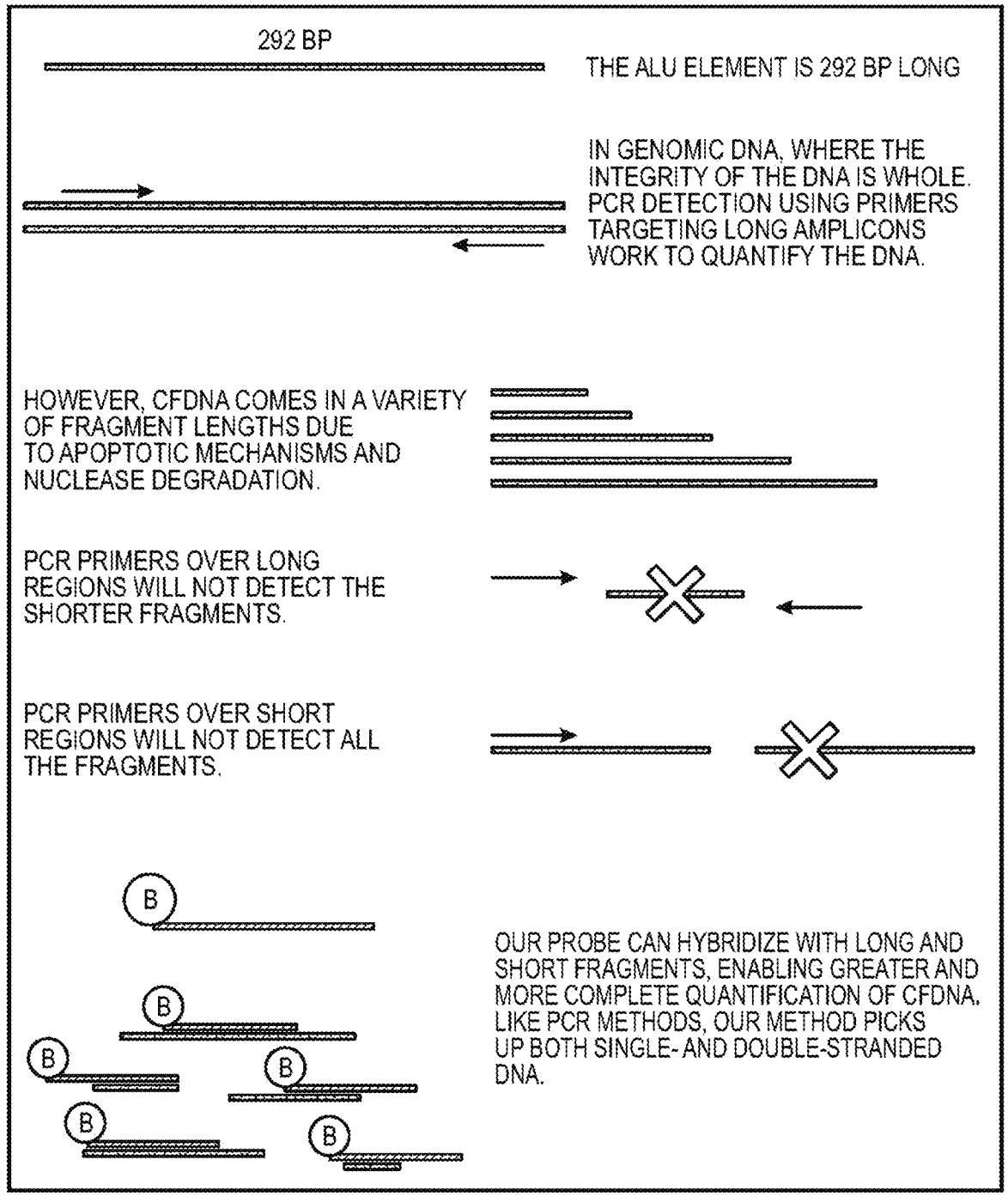
FIG. 2 compares using the methods disclosed herein and using the standard PCR based methods in Alu detection for cfDNA analysis.

To provide more complete coverage of the cfDNA repertoire in the biofluid, a length of <100 bp were selected for the nucleic acid probe targeting the Alu repeats so that both long and very short fragment lengths of cfDNA could be captured. In this particular assay, the probe length was 81 bp (FIG. 2), although a shorter length, such as that commonly employed by PCR primers of 18-22 bp should work as well.

Reference ALU sequence (SEQ ID NO:1) is listed below and the 81 bp site (SEQ ID NO:2) targeted for the Alu probe is highlighted in bold.

5'GGCCGGGCGCGGTGGCTCACGCCTGTAATCCCAGCACTTTGGGAGGC

CGAGGCGGGCGGATCACCTGAGGTCAGGAGTTCGAGACCAGCCTGGCCA

ACATGGTGAAACCCCGTCTCTACTAAAAATACAAAAATTAGCCGGGCGT

GGTGGCGCGCGCCTGTAATCCCAGCTACTCGGGAGGCTGAGGCAGGAGA

ATCGCTTGAACCCGGGAGGCGGAGGTTGCAGTGAGCCGAGATCGCGCCA

CTGCACTCCAGCCTGGGCGACAGAGCGAGACTCCGTCTCAAAAAAA

A-3'

Biotin was selected due to wide availability of reagents that are compatible. However, any number of amplification schemes, such as digioxigenin-anti-digioxigenin antibodies or even direct HRP conjugation would work.

Dual biotinylated-oligonucleotide complementary to the Alu element was designed and synthesized (52-Biotin/GCCTGTAATCCCAGCTACTCGGGAGGCTGA
GGCAGGAGAATCGCTTGAACCCGGGAGGCGGAGGTTGCAGT-
GAGCCGAGAT
(SEQ ID NO: 2))

Figure 3:
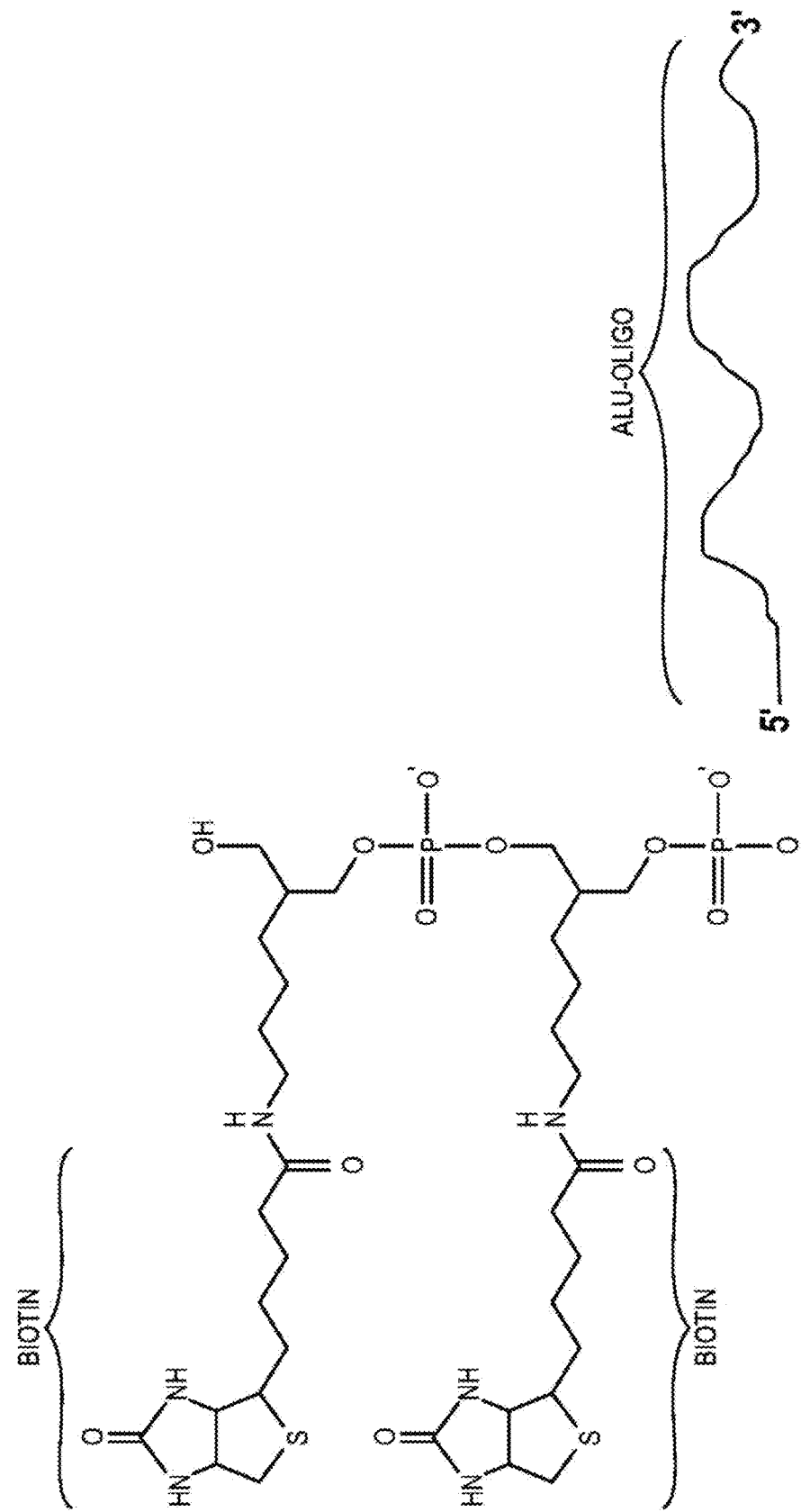
FIG. 3 shows a dual biotinylated-oligonucleotide complementary to the Alu repeats.

This was used to quantify cfDNA using a chemiluminiscence based detection system using streptavidin-HRP and chemiluminescent substrate (SuperSignal™ ELISA Femto Substrate) solutions (FIG. 3).

Chemiluminescence was chosen because it is the most sensitive method available in a microwell for HRP detection (FIG. 4), although colorimetric and fluorometric methods will work. Colorimetric methods have also proved satisfactory. However, colorimetric methods also take longer to incubate and produce results.

Example 2. Testing the Effectiveness of the DNA Stabilization Solution

Figure 1B:
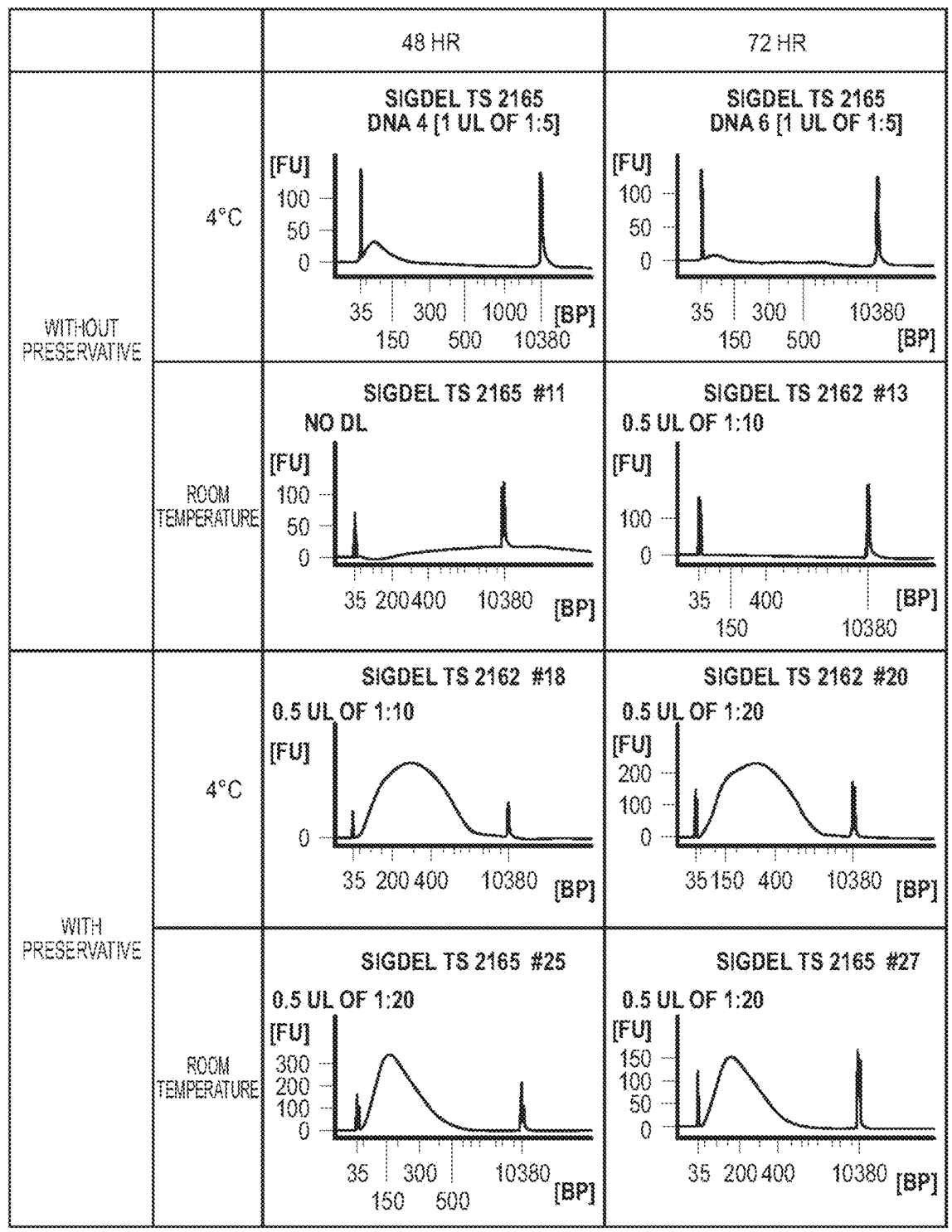

In order to test the effectiveness of DNA stabilization solution in urine containing sonicated genomic DNA, we purified genomic DNA from whole blood using QiaAMP DNA Blood Mini Kit (Qiagen), and sonicated it for 10 min using a Model 550 probe Sonic Dismembrator (ThermoFisher Scientific) on intensity setting 3. Cycles were set at 10 seconds on and 20 seconds off. Samples were run on 1% gel electrophoresis to establish fragment sizes approx. 150 to 250 base pairs obtained. With sonication, we achieved DNA fragments of approximately 150 to 250 base pairs in size, a range that best represents cfDNA in transplant rejection (FIGS. 1A and 1B). Next, we formulated a preservation solution containing 10 g/L Diazolidinyl Urea, 20 g/L polyethelyene glycol, 1 mM aurintricarboxylic acid, 10 mM K2EDTA, 10 mM sodium azide, and 1× phosphate buffered saline, pH7.4. An experiment was designed to test the effectiveness of DNA preservation solution in preserving the integrity of DNA. Fragmented genomic DNA (approx. size-150 to 250 base pairs) was added to 1000 μL tubes containing urine with and without preservation solution. The experiment was run in parallel at 4° C. and at room temperature. FIGS. 1A and 1B show-electropherograms that demonstrate how in the absence of DNA preservative solution the DNA degrades and disintegrates completely over a period of 72 hours, whereas DNA preservation solution helps maintain DNA integrity up to 72 hours.

Example 3. Determine the Acute Rejection Status for Kidney Transplant Patients a. Sample collection Urine samples from three patients (patient #1-#3) having received kidney transplant were collected, mid-stream, in sterile containers at different time points during the period post transplantation. The urine samples from patient #1 were taken at day 1, 16, 22, 51, and 180; urine samples from patient #2 were taken at day 23, day 41, and day 103; and urine samples from patient #3 were taken at day 100, day 132, day 185, and day 337. At a listed time point, in addition to collection of urine, a biopsy is taken to confirm the acute rejection. For example, the listed time point for patient #1 in this study is day 22. The urine sample was aliquoted into 2 mL for extraction with the QiaAmp® Circulating Nucleic Acids Kit (Qiagen) following the manufacturer's instructions with an elution volume of 20 μl in H$_2$O.

Using a white, opaque ELISA plate such as the 96-well LUMITRAC 600 (Greiner Bio-One), 5 microliters of the eluted cfDNA were plated onto the plate, either in singlicate, duplicate, or triplicate as needed. To these sample wells, 10 microliters of a 5×PBS and 0.5 M MgCl$_2$ buffer were added and then 35 microliters of molecular grade H$_2$O was added for a total of 50 microliters per well. To create a standard curve, known quantities of human DNA extract were added in duplicate in a titration series of 1:3 from 200,000 to ~12 GE/mL, where a GE (genomic equivalent) is defined as 6.6 pg of human DNA. This was also in the same buffer, a final working concentration of 1×PBS and 0.1 M MgCl$_2$.

The cfDNA plate was incubated overnight at 4 C or for a minimum of 2 hours at RT shaking at 300 RPM. The liquid was then discarded and the plate was dried via patting against absorbent paper towels. The plate was then blocked in 5% BSA in PBS with 300 microliters per well, for a minimum of 1 hour at RT shaking at 300 RPM. The liquid was then discarded and the plate was dried via patting against absorbent paper towels. The plate was then incubated in 50 microliters of our double-biotinylated Alu oligonucleotide probe diluted in the 5% BSA at a concentration of 35.56 ng/microliters. This was allowed to incubate for a minimum of 1 hour at RT shaking at 300 RPM. The liquid if then discarded and then the wells were washed with 300 microliters of 1×PBS three times. The wash was then discarded and the plate was dried via patting against absorbent paper towels. The plate was then incubated in 50 microliters of streptavidin-HRP diluted 1:200 per manufacturer's instructions in 5% BSA and allowed to incubate for no more than 1 hour at RT shaking at 300 RPM. The liquid is then discarded and then the wells were washed with 300 microliters of 1×PBS three times. The wash was then discarded and the plate was dried very thoroughly via patting against absorbent paper towels. 150 µl of SuperSignal ELISA Femto chemiluminescent substrate solution (ThermoFisher) was then added to each well. The plate was analyzed upon 1 minute of mixing based on total luminescence.

The generated values were then regressed using a 5-parameter sigmoid curve fit, such as that provided in GraphPad Prism and the resultant cell-free concentration values were corrected for the dilution done in the microwell as well as the concentration done from 2 mL of urine to 20 µl of eluate.

Creatinine was measured using the QuantiChrom Creatinine Assay Kit (BioAssay Systems) according to manufacturer's instructions.

b. Determining the Cutoff Value of cfDNA/Creatinine Ratio

Figure 7:
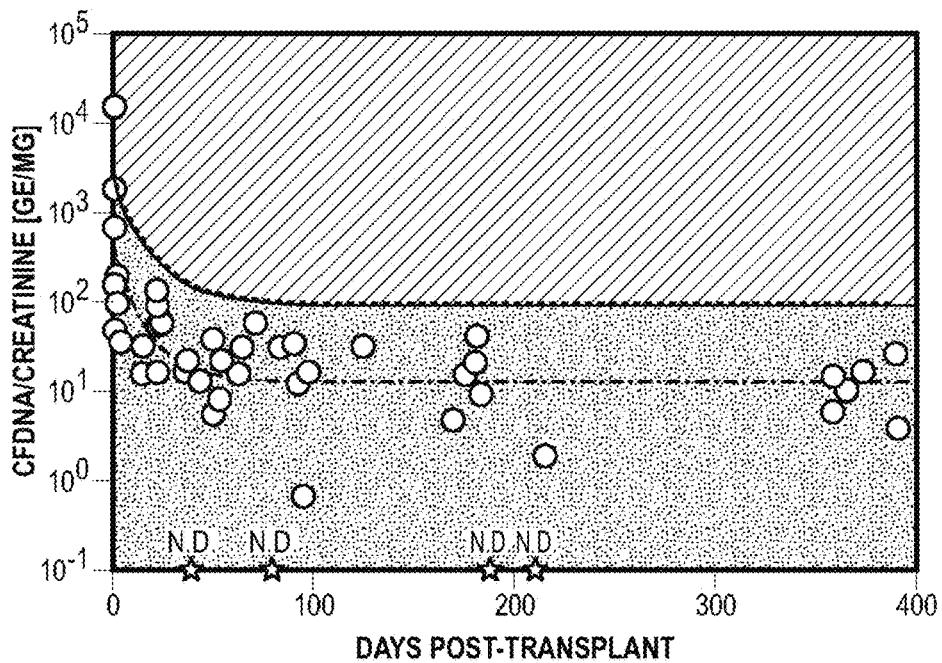
FIG. 7. shows an exponential decay curve showing change of cfDNA/creatinine ratio over the number of days post-transplantation using data from 9 patients who received kidney transplant and did not experience acute rejection episodes.

Prior to the study involving patients #1-#3, cutoff values of cfDNA/creatinine ratios were established based on data from nine (9) patients, who received kidney transplant and did not have kidney injury as confirmed by biopsy. cfDNA and creatinine amounts from urine samples from these 9 patients were determined as described herein. The urine creatinine values were first converted to mg/mL and the cell-free DNA values are divided by this creatinine measurement to produce cfDNA/creatinine with units of [GE/mg], wherein a GE (genomic equivalent) is defined as 6.6 pg of human DNA. The cfDNA/creatinine ratio vs. the days post transplantation was plotted as shown in FIG. 7 and a 95% prediction band (the dotted line) as dependent on time-post-transplant was modeled as an exponential decay curve with following equation.

cfDNA/Creatinine [GE/mg]=10^((5.612−4.007)*EXP(−0.05977*(Days Post-Transplant))+4.007)/100.

Figure 9B:
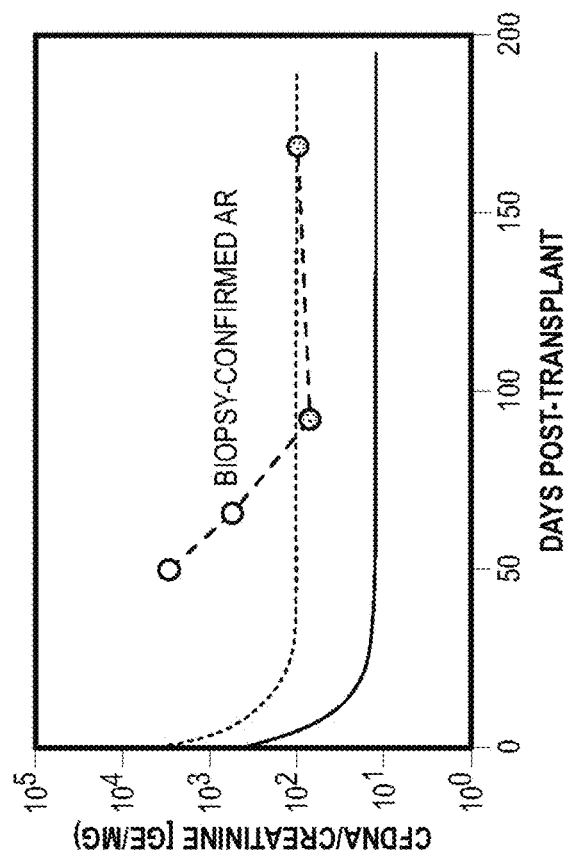
FIGS. 9A and 9B show using the cfDNA/creatinine ratio to predict acute rejection in patient #2 and patient #3.
Figure 9A:
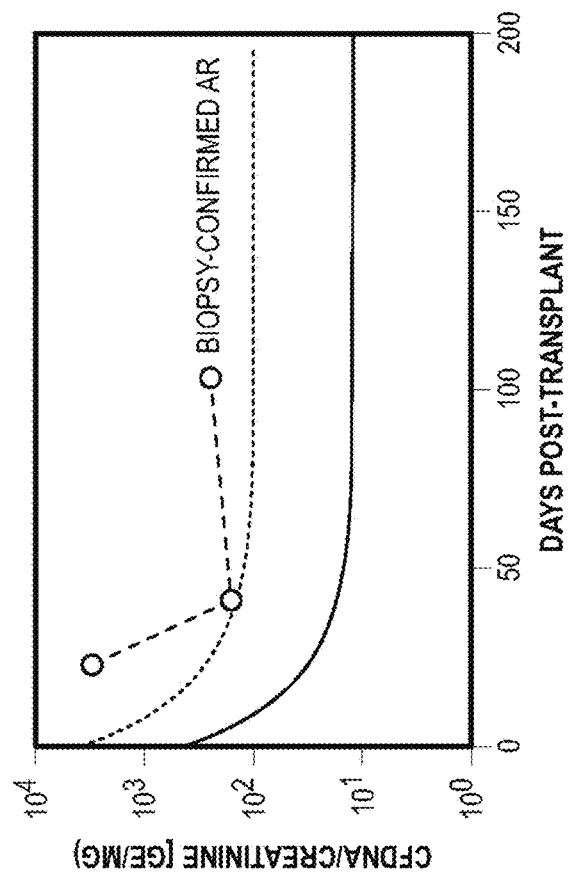
Figure 11:
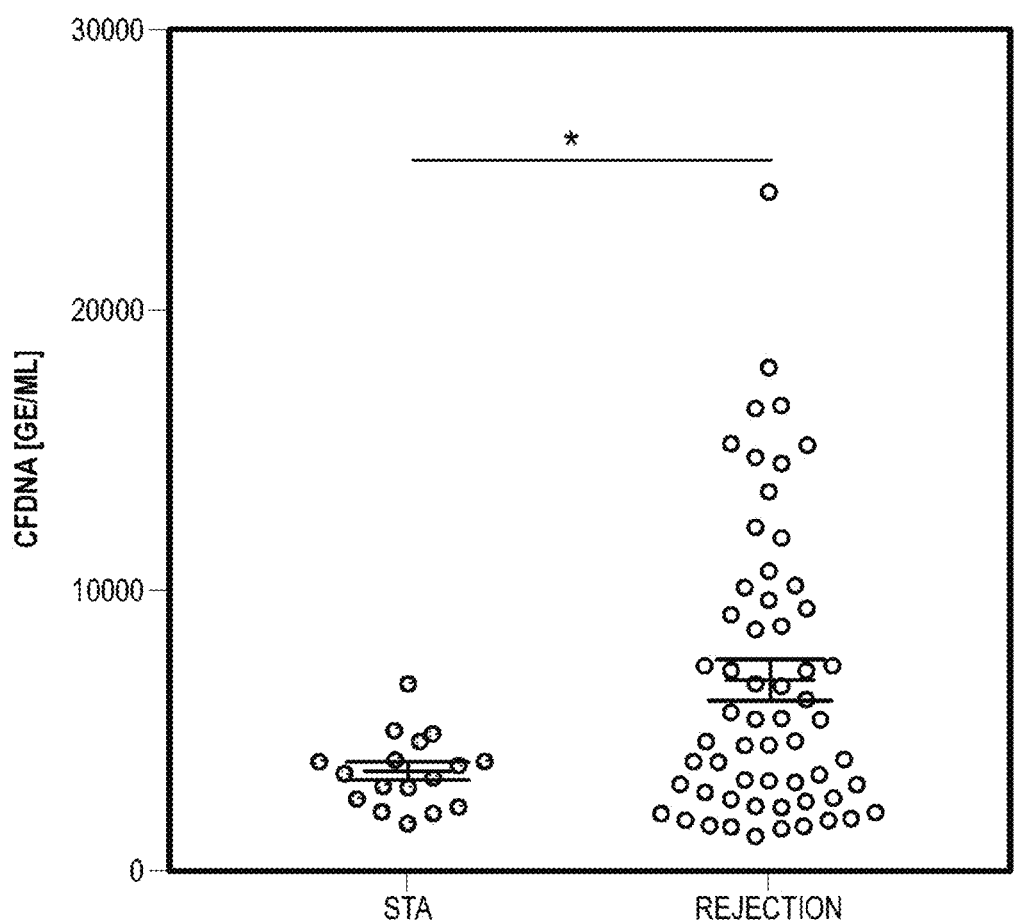
FIG. 11 shows a comparison between the cfDNA concentration found in bronchoalveolar lavage (BAL) fluid from individuals who had stable lung transplants ("STA") and from those who underwent occult, acute, or chronic rejection ("Rejection"). The p-value was 0.0427.

Each data point in this one-sided 95% prediction interval corresponds to the estimate of the upper limit of the cfDNA/creatinine ratios that, with 95% confidence, is predicted to be higher than cfDNA/creatinine ratios from 95% of future non-rejecting patients at the same time point post-transplantation. The urine creatinine values were first converted to mg/mL and the cell-free DNA values are divided by this creatinine measurement to produce cfDNA/creatinine with units of [GE/mg]. The cfDNA/creatinine ratio was plotted against days post transplantation. FIG. 8A. KIT prediction scores were calculated as described above, and plotted against days post-transplantation. FIG. 8B. Although between the first and second points the cfDNA/creatinine ratio drops (FIG. 8A), the prediction score showed that that relative risk actually increases prior to the biopsy-confirmed acute rejection episode (FIG. 8B) KIT was above zero at time point 22, indicating that patient #1 had kidney injury and acute rejection episodes. The acute rejection status was confirmed by the examining the biopsy taken at the listed time point. Patients #1-#3 were all given an immunosuppressant after the listed time points: Tacrolimus, MMF, steroids to patient #1, Tacrolimus, MMF, Steroids to patient #2, and Tacrolimus and Sirolimus to patient #3.

cfDNA/creatinine ratios of patients #2-#3 for urine samples were plotted against days post-transplantation. FIGS. 9A and 9B. For both patients, acute rejections were predicted using the method disclosed herein at a time point prior to listed time point, when they were confirmed by biopsy. Additionally, as shown in FIG. 9B, the administration of an immunosuppressant from the listed time point thereon caused the cfDNA ratio to decrease into the stable region, indicating successful treatment Clinical determinants of graft injury can be made on the basis of an absolute elevation in the cfDNA value above the determined threshold as well as an increase in the cfDNA burden over time using patient specific threshold data. A graft injury is presumed to result from sub-optimal immunosuppression exposure, an abnormal, elevated cfDNA result could trigger the following clinical actions:1) return of patient to clinic for closer follow-up; 2) consider an earlier protocol biopsy in a patient scheduled to have one; 3) consider an indication biopsy to evaluate for sub-clinical acute rejection and/or other cause of graft injury; 4) a change in immunosuppression drug type or dosing. Conversely, a low, stable cfDNA result could trigger the following clinical actions: 1) reduce clinic follow-up frequency; 2) avoid unnecessary protocol biopsies that are done to look for sub-clinical graft injury; 3) change in immunosuppression drug type or dosing.

Example 4. Of Determining the Rejection Status for Lung Transplant Patients

Bronchoalveolar lavage (BAL) fluid samples from 76 patients having received lung transplants were collected in sterile containers either during stable period or during rejection episodes. The BAL fluid was aliquoted into 400 µL for extraction with the QIAamp Circulating Nucleic Acids Kit (Qiagen) following the manufacturer's instructions with an elution volume of 20 µL in H$_2$O. The cfDNA was measured as disclosed in Example 2.

The generated values were regressed using a 5-parameter sigmoid curve fit, such as that provided in GraphPad Prism and the resultant cell-free concentration values were corrected for the dilution done in the microwell as well as the concentration done from 400 µL of BAL fluid to 20 µL of eluate.

The normalized cfDNA concentrations from BAL fluid were compared between stable and rejection patients. FIG. 10. The mean level of cfDNA in the rejection patients was significantly higher than in the stable patients. An abnormal, elevated cfDNA result could trigger similar clinical actions as disclosed in Example 2.

Example 5. Determining Kidney Injury Status Using a KIT Score

FIG. 13 provides an illustrative embodiment, which displays a IT score for assessing kidney injury ("KIT") based on a dataset of 490 clinical patient samples with multiple causes of kidney injury. The resulting KIT score was based on a subset of 299 clinical patient samples that had complete measurements of cfDNA, creatinine, CXCL10, Clusterin, Protein, and DNA methylation markers; 111 type II diabetes mellitus, 71 immune, 50 kidney stones, 20 transplant rejections, 19 hypertension and 28 controls. The resulting KIT score had over 91% sensitivity and specificity for detection of kidney injury (AUC=96.9%). FIGS. 14A-E provide results of generalized linear model fits and associated ROC curves. These results illustrate that in addition to displaying the probability of kidney injury, the underlying algorithm can accurately provide the probability of kidney injury due to each disease cause; namely, type II diabetes mellitus, immune response, kidney stones, transplant rejection, and hypertension. For these data, the resulting algorithm showed an over 92% sensitivity and specificity (AUC>99.4%) for detection of each cause of kidney injury.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

What is claimed is:

1. A method of preparing a urine sample for detection of kidney injury, the method comprising:
   (i) obtaining the urine sample and preparing the urine sample for detection of kidney injury by:
   (ii) contacting cfDNA from the urine sample with a detection reagent to measure cfDNA from the urine sample and measuring an amount of the cfDNA contacted with the detection agent, wherein the detection reagent is a nucleic acid probe comprising a nucleotide sequence for hybridizing to at least 70 continuous nucleotides of an ALU sequence in the cfDNA, wherein the 3' or the 5' end of the nucleic acid probe is covalently linked to a detectable label;
   (iii) contacting an inflammation marker from the urine sample with a detection reagent to measure the inflammation marker from the urine sample and measuring an amount of the inflammation marker contacted with the detection reagent, wherein the inflammation marker is a CXCL10 protein, wherein the detection reagent for the inflammation marker is an antibody thereto;
   (iv) contacting creatinine from the urine sample with a detection reagent to measure creatinine from the urine sample and measuring the amount of creatinine contacted with the detection reagent, wherein the detection reagent for the creatinine is a colorimetric reagent;
   (v) contacting total protein from the urine sample with a detection reagent to measure the protein from the urine sample and measuring the protein contacted with the detection reagent, wherein the detection reagent for the total protein is a colorimetric reagent;
   (vi) contacting methylated DNA from the urine sample with a detection reagent to measure methylated DNA from the urine sample and measuring the methylated DNA contacted with the detection reagent, wherein the detection reagent for the methylated DNA is an antibody that detects 5-methylcytosine; and
   (vii) contacting clusterin from the urine sample with a detection reagent to measure clusterin from the urine sample and measuring the clusterin contacted with the detection reagent, wherein the detection reagent for the clusterin is an antibody thereto;
   thereby preparing the urine sample for the detection of kidney injury.

2. The method of claim 1, further comprising inputting each one of the measurements obtained from steps (ii)-(vii) into a model to produce a score indicative of kidney injury.

3. The method of claim 2, further comprising detecting kidney injury using the score with an area under the receiver operating character curve (AUC) of at least 85%.

4. The method of claim 3, wherein the model is produced by evaluating different subjects afflicted with one or more of focal segmentosa glomerulosclerosis (FSGS), IgA nephropathy, diabetic kidney disease, BK viral nephritis, glomerulonephritis, acute tubular necrosis (ATN), IgA disease, or transplant rejection.

5. The method of claim 2, wherein the linear model is produced by evaluating at least 400 samples in a machine learning model.

6. The method of claim 2, wherein the score is a composite value representative of a probability estimate for kidney injury.

7. The method of claim 2, wherein the score is scaled from 0-100.

8. The method of claim 1, wherein the urine sample is stabilized with a stabilizing solution prior to steps (ii)-(vii).

9. The method of claim 8, wherein the stabilizing solution comprises a formaldehyde donor and a chelator in a concentration sufficient to inhibit cell lysis and to inhibit nucleases in the urine sample.

10. The method of claim 1, wherein the nucleic acid probe forms an immobilized cfDNA/nucleic acid probe complex.

* * * * *